United States Patent [19]

Shah et al.

[11] Patent Number: 5,382,515
[45] Date of Patent: Jan. 17, 1995

[54] CREATIVE KINASE-MB IMMUNOASSAY FOR MYOCARDIAL INFARCTION AND REAGENTS

[75] Inventors: Vipin D. Shah, Saratoga; Shing-Erh Yen, Foster City, both of Calif.; Gerald M. Anchin, Bellaire, Tex.

[73] Assignee: International Immunoassay Laboratories, Inc., Santa Clara, Calif.

[21] Appl. No.: 83,853

[22] Filed: Jun. 25, 1993

Related U.S. Application Data

[63] Continuation of Ser. No. 467,837, Jan. 19, 1990, abandoned, which is a continuation-in-part of Ser. No. 299,277, Jan. 23, 1989, Pat. No. 5,202,234, which is a continuation-in-part of Ser. No. 76,038, Jul. 21, 1987, Pat. No. 4,900,662.

[51] Int. Cl.$^6$ ............... G01N 33/573; G01N 33/53; C07K 15/28
[52] U.S. Cl. ................... 435/7.4; 435/7.6; 435/7.92; 435/17; 435/172.2; 435/240.27; 436/524; 436/528; 436/811; 436/815; 436/536; 530/387.1; 530/388.1; 530/388.26; 530/389.3
[58] Field of Search .............. 435/7.1, 7.4, 7.6, 7.92, 435/17, 172.2, 240.27, 810; 436/524, 528, 531, 538, 547, 548, 811, 815, 830; 935/110; 530/387.1, 388.1, 388.26, 389.3

[56] References Cited

U.S. PATENT DOCUMENTS

| | | | |
|---|---|---|---|
| 4,067,775 | 1/1978 | Wurzbury et al. | 195/99 |
| 4,205,057 | 5/1980 | Whitaker | 436/804 X |
| 4,267,271 | 5/1981 | Roberts | 435/7.4 |
| 4,353,982 | 10/1982 | Gomez et al. | 435/7.4 |
| 4,624,916 | 11/1986 | Shah et al. | 435/7.4 |
| 4,722,903 | 2/1988 | Kudryk et al. | 435/7 |
| 4,810,639 | 3/1989 | Pankratz | 435/174 |
| 4,900,662 | 2/1990 | Shah et al. | 435/7.4 |
| 4,912,033 | 3/1990 | Ladenson et al. | 435/7.4 |
| 5,009,997 | 4/1991 | Shah et al. | 435/7.4 |
| 5,047,354 | 9/1991 | Foegh et al. | 436/536 |
| 5,202,234 | 4/1993 | Shah et al. | 435/7.4 |

FOREIGN PATENT DOCUMENTS 339814 11/1989 European Pat. Off.
8600992 2/1986 WIPO.

OTHER PUBLICATIONS

D. Armbruster, "The Genesis and Clinical Significance of Creative Kinese Isoforms", Laboratory Medicine vol. 22, May 1991 pp. 325–334.
Yen et al, Clinical Chemistry vol. 35, No. 6, Abstract 260 (1989) p. 1121.
Chemical Abstract 107(5): 35431, "Analysis of Creative Kinase Isoenzymes and Isoforms in Serum . . . After Acute Myocardial Infarction".
Chemical Abstract 103(13): 102845, "Early Detection of Myocardial Infarction . . . By Analysis of Plasma MM Creative Kinase Isoforms".
Chemical Abstract 102(3): 22264, "Creative Kinase MM Isoenzyme Subforms in Myocardium . . . ".
Morison et al, "Effect of Creative-Kinase-MM Subtype Composition on a CK-MB Immunoinhibition Assay", CLin. Chem. 34(3) 535-8 (1988).

(List continued on next page.)

Primary Examiner—Toni R. Scheiner
Attorney, Agent, or Firm—Skjerven, Morrill, MacPherson, Franklin & Friel

[57] ABSTRACT

Methods and reagents for determining the lapse of time since an acute disease event, such as the occurrence of a myocardial infarction, are presented. A serum or plasma sample is assayed to determine the concentration of two different analytes selected from a group of creatine kinase-MB species. From these measurements, the time of the acute event can be more accurately determined. Novel antibodies, labeled and insolubilized derivatives of these antibodies, labeled proteins, and kits containing one or more of these reagents are also described.

9 Claims, No Drawings

OTHER PUBLICATIONS

Suzuki et al, "Monoclonal Antibody Inhibiting Creative Kinase MM$_3$ but not Isoform MM,", *Clin. Chem.*, 36(1) 153-6 (1990).

Medline Abstract 75189008 Dolken et al, "Immunofluorescent Localization of Glycogenolytic and Glycolytic Enzyme Proteins and of Malate Dehydrogenase Isozyme . . . " *Histochemistry* (1975) 43(2) 113-21.

Falter et al., "Studies on the Sub-Banding of Creatine Kinase MM and the 'CK Conversion Factor'", *Clin. Biochem.* 14:3-7 (1981).

Tijssen, *Practice and Theory of Enzyme Immunoassays* ix-xx (Elsevier 1985)

Wu, "Creatine Kinase Isoform Analysis", *Clin. Chem. News* Jun. (1991).

*Analytical Biochemistry*, (1985), 149, pp. 209-217, "Sensitive Quantification of Isoforms of Canine MM Creatine Kinase With an Immunoblot . . . ", Grace et al.

*Circulation*, (1986), 74, pp. 105-109, "Diagnostic Changes In Plasma Creatine Kinase Isoforms Early After The Onset Of Myocardial Infarction", Jaffe et al.

*Biochemica Et Biophysica Acta*, (1984), 790, pp. 230-237, "Purification of Five Creatine Kinase-MM Variants From Human Heart and Skeletal Muscle", Vaidya et al.

*Clinical Chemistry*, (1987), 33, pp. 986-987, "Monoclonal Antibodies Specific For the CK-M Subunit and the CKMM Dimer", Daiss.

*Clinical Chemistry*, (1988), 34, p. 1279, "A Monoclonal Antibody Inhibiting Creatine Kinase-MM3, But Not MM1 Sub-Type", Suzuki et al.

*Clinical Chemistry*, (1989), 35, pp. 493-494, "Two Commercial Test Kits For CK-MM Isoforms Evaluated For Early Recognition of Acute Myocardial . . . " Shah et al.

CREATIVE KINASE-MB IMMUNOASSAY FOR MYOCARDIAL INFARCTION AND REAGENTS

RELATIONSHIP TO COPENDING APPLICATION

This application is a continuation of application Ser. No. 07/467,837, filed Jan. 19, 1990, now abandoned, which application is a continuation-in-part of copending application Ser. No. 299,277, filed Jan. 23, 1989, now U.S. Pat. No. 5,202,234, which application is a continuation in part of application Ser. No. 76,038, filed Jul. 21, 1987, now U.S. Pat. No. 4,900,662.

FIELD OF THE INVENTION

The invention herein relates to the immunological diagnostic measurement of biological markers which are acted upon by endogenous conversion factors, and which are released into body fluids at the onset of an acute disease incident. More specifically, the invention relates to the immunologic measurement and calculation of a ratio two or more biological markers, which may or may not be related, to diagnose and estimate the length of time since the acute incident In another embodiment, the invention herein also relates to an improved method for immunological diagnosis of myocardial infarction.

BACKGROUND OF THE INVENTION

Diagnosis of acute disease is often based on abnormal levels of disease markers, such as enzymes and hormones in biological fluids such as serum, particularly when the concentration changes quickly during the acute phase of disease. For example, the enzyme creative kinase (CK, ATP:creatine N-phosphotransferase) catalyzes the reversible transfer of a phosphate group from ATP to creatine. It exists as a dimer composed of two subunits commonly identified as the M-subunit and the B-subunit. CK-MB is associated with acute myocardial infarction, and is present in serum in only trace concentrations in the absence of such an episode. Appearance of CK-MB isoenzyme in serum is therefor indicative of myocardial infarction. CK-MM isoeforms are present in the serum of normal patients in measurable amounts, but are present in significantly increased concentration following acute myocardial infarction. Assays to determine the occurrence of an acute myocardial infarction by measuring CK isoenzymes are known.

The biological activity and physical properties of proteins such as enzymes and hormones are determined by structural features of the molecule. These features are often modified by endogenous conversion factors present in body fluids. Such conversion may or may not cause the loss of biological activity, or changes in physical properties such as electrophoretic mobility of the molecule. The conversion products may coexist with the original molecule immediately following the onset of an acute disease, but with the passage of time, one finds only the altered protein in the body fluids.

Many tests have been developed which immunologically measure a protein marker in a body fluid. Such immunoassays are often not selective in differentiating native forms of the analyte from altered forms of the analyte. For example, both native and altered forms of CK-MM are immunologically measured using anti-(CK-MM) antibody. Bioassay techniques have been traditionally used to measure enzyme activity. When the altered form of the enzyme marker is inactive, the measurement of enzyme activity provides an adequate measure of changes which occur in the level of the active enzyme in the system. Immunoassays, while offering a more convenient approach, are dependent upon having antibodies which bind selectively with the moiety to be measured. When the altered protein product differs only slightly from a native marker protein, antibodies may be unable to distinguish between the native form and the altered form and will react with both moieties, giving an erroneous result. Immunoassay efforts have generally addressed development of antibodies which bind specifically with the native protein marker together with its altered forms, antibodies binding with only the derivative forms generally being avoided.

DESCRIPTION OF THE PRIOR ART

At the onset of acute myocardial infarction (AMI), disease markers including several isoenzymes of CK are released from damaged myocardial tissues and enter the circulating blood. The amounts of CK-MB and CK-MM are known to increase in circulation after the onset of AMI. With some exceptions, the levels of both CK-MM and CK-MB become abnormal within 3-6 hours after the onset of AMI. Other markers released by AMI are myoglobin, myosin, lactate dehydrogenase, citrate synthetase and myosin light chains. These later markers offer some advantage over CK-MB measurements because the CK-MB does not peak until 18-24 hours after the onset of chest pain, in the absence of thrombolytic agent treatment.

CK-MMA, the isoform of CK-MM present in a tissue such as myocardium tissue, is a homodimer of two M chains, each with a terminal lysine group (Jaffe et al, Circulation 74(1):105-109 (1986)). After release of CK-$MM_A$ into plasma, the terminal lysine group from one chain is rapidly removed by a conversion factor which has not yet been identified, yielding CK-$MM_B$, an isoform with a terminal lysine group on one chain. Subsequent cleavage of the other terminal lysine group yields a third isoform, CK-$MM_C$, the major ultimate form.

Several conflicting nomenclatures have been used to designate the various isoforms of CK-MM, and the nomenclature used in this patent is that suggested by Jaffe et al (supra). Creatine kinase isoenzyme CK-MM has been resolved into at least three enzymatically active isoforms, designated CK-$MM_A$, CK-$MM_B$, and CK-$MM_C$. CK-MB has been further resolved into two enzymatically active isoforms by electrophoresis (CK-$MB_A$ and CK-$MB_B$), as reported by Weaver et al, Clin. Chem. Acta. 75:377 (1977); Chapelle et al, Clin. Chem. 26:457–462 (1980); Yasmineh et al, J. Lab. Clin. Med. 98:109–118 (1981); Falter et al, Clin. Biochem. 14:3–7 (1981); George et al, J. Biol. Chem. 259:2667–2674 (1984); and Panteghini et al, Clin. Chem. Acta. 155:1–10 (1986). The serum concentrations of the CK-MM isoforms versus time following a myocardial infarction have been studied by Morelli et al, Circulation 67(6):1283–1289 (1983); Hashimoto et al, Circulation 71(2):363–369 (1985); Jaffe et al, Circulation 74(1):105–109 (1986); and Wu et al, Clin. Chem. 33(3):358–362 (1987), and several of these authors suggest that the analysis of CK-MM subtypes could be useful in the early diagnosis of acute myocardial infarction, even though CK-MM isoforms exist in the serum of patients who are not suffering from acute myocardial infarction.

U.S. Pat. No. 3,932,221 describes the use of immunoprecipitation procedures for determining isoenzyme levels in body tissues or fluids using isoenzyme-antibody complexes, and lists most types of body enzymes including creatine kinase as a suitable object for this approach. No CK-binding antibodies which can differentiate altered forms of CK-MM are disclosed in the patent. U.S. Pat. No. 4,105,499 describes column chromatographic separation of CK-MB from serum for rapid detection of a heart attack, and U.S. Pat. No. 4,046,634 discloses separation of CK isoenzymes by ion exchange chromatography. U.S. Pat. No. 4,260,678 describes an affinity column procedure for determining creatine kinase enzymes in serum using immobilized antibodies specific for CK-MM or CK-BB, and testing the immobilized enzyme for activity.

SUMMARY OF THE INVENTION

The method of this invention for determining the lapse of time since an acute disease event comprises (a) immunologically determining the plasma or serum concentration of a first and a second analyte set, each set comprising at least one selected from the group consisting of a transiently elevated substance, its endogenously altered forms, and combinations thereof; wherein the first and second analyte sets are not the same; and (b) determining the ratio of the first and second analyte sets. The ratio of the first and second analyte sets provides an indication of the lapse of time since the occurrence of the acute episode.

The first and second analyte sets can determine related or unrelated individual substances which have been empirically determined to provide the information desired. In a preferred embodiment, MI-$P_A$, a protein related to myocarcial infarction having enzymatic activity, and MI-$D_B$, a protein related to myocardial infarction, are determined.

Alternatively, the first and second analyte sets can determine a family of substances which are related as being a transiently elevated substance and derivative isoforms of that substance which have been altered by endogenous conversion factors. In a preferred embodiment, isoforms of CK-MM, such as total CK-MM, and CK-$MM_C$ or isoforms of CK-MB, such as CK-$MB_B$ and total CK-MB are immunologically measured.

Another aspect of the invention herein is an immunoassay to determine the occurrence of a myocardial infarction. Hybridomas, labeled reagents and kits for determining occurrence and lapsed time since an AMI are also disclosed.

DETAILED DESCRIPTION OF THE INVENTION

The method herein relates to the immunological measurement of a first analyte set and a second analyte set, in a liquid specimen from a patient believed to have suffered from an acute disease event. Each analyte set comprises at least one selected from a group consisting of a transiently elevated biological substance and its endogenously altered forms, wherein the first and second analyte sets are not the same. The first and second transiently elevated substances can be different, such as a measurement of the transiently elevated substance MI-$P_A$, which is believed to be degraded by endogenous conversion factors derivative products termed to MI-$P_B$ and MI-$P_C$; and a measurement of a substance termed MI-$D_B$, which is believed to be the derivative product of the transiently elevated substance MI-$D_A$.

Alternatively, the first and second transiently elevated substances can be the same, an example being the measurement of isoforms of CK-MM or CK-MB. In a preferred embodiment, at least one of the analyte sets includes a transiently elevated substance, the other includes an endogenously altered form of a transiently elevated substance and not more than one of the sets includes a transiently elevated substance and an endogenously altered form. The first and second sets are not the same, but each different set is selected from the group consisting of CK-$MM_A$, CK-$MM_B$, CK-$MM_C$, and mixtures thereof or CK-$MB_A$, CK-$MB_B$ and mixtures thereof.

Immunological methods are most convenient for carrying out the assays of this invention because of their specificity, and the term "immunoassays" as used herein is defined to mean any method using a preferential binding of an antigen with a second material (i.e., a binding partner, usually an antibody or antibody fragment having an antigen binding site) which binds preferentially with an epitope of the antigen. Preferential binding as used herein refers to binding between binding partners which is selective and generally specific. Included within the scope of this invention are all immunoassays including this step, including but not limited to sandwich, competition, dip stick, immunoagglomeration, immunoextraction, immunoprecipitation, immunodiffusion, immunoinhibition, transistor bridge probe, particle sorting, light disturbing, light scattering, and ultrasonic probe immunoassays, for example.

A "transiently elevated substance", as used herein, is a biological substance such as a protein, glycoprotein, enzyme, etc., which is released in significantly increased quantities at the occasion of an acute disease event such as a heart attack, stroke, or at the occasion of a traumatic injury such as a broken bone or a hematoma; which is not normally present in such increased quantities; and which is broken down over time by endogenous conversion factors. A variety of acute disease events can be measured using the methods taught herein. However, for purposes of clarity and not by way of limitation, the invention will be further described with reference to the situation wherein the acute disease event is myocardial infarction.

"Derivative substances", as used herein, are altered forms of a transiently elevated biological substance which have been acted upon by one or more endogenous conversion factors.

A "family" of substances, as used herein, refers to a transiently elevated substance and its derivative isoforms.

The term "isoform" refers to each of the transiently elevated substance and any derivative substances produced by action of endogenous conversion factors upon the transiently elevated substance. For example, when the family of transiently elevated substances is MI-P, MI-$P_A$ is a transiently elevated substance, and MI-$P_B$ is a derivative substance. Each of MI-$P_A$ and MI-$P_B$ are isoforms of MI-P. A combined isoform comprises two or more isoforms, i.e., MI-$P_{A+B}$. When the family of transiently elevated substances is CK-MM, CK-$MM_A$ is a transiently elevated substance, and CK-$MM_B$ and CK-$MM_C$ are derivative substances. Each of CK-$MM_A$, CK-$MM_B$ and CK-$MM_C$ are isoforms.

In an acute disease process which is amenable to analysis by this invention, a transiently elevated substance will be released in a significant quantity at the time of the acute disease event of interest. The initial elevated concentration will decrease as endogenous conversion factors act upon the initial transiently elevated substance. Substances derived therefrom by the action of endogenous conversion factors will thereafter each be transiently elevated in a serial manner, as each is first created then metabolized by endogenous conversion factors.

The term "antibody" as used herein is defined to include antibodies of classes IgG, IgM, IgA, IgD, and IgE, and fragments and hybrid derivatives of antibodies including Fab, and F(ab')$_2$ fragments of antibodies. The term "anti-(MI-P$_A$) antibody" is defined herein to designate an antibody which binds selectively with MI-P$_A$ protein. The term "anti-(MI-D$_B$) antibody" is defined herein to designate an antibody which binds selectively with MI-D$_B$ protein having enzymatic activity. The term "anti-(CK-MM$_A$) antibody" is defined herein to designate an antibody which binds selectively with CK-MM$_A$ and which does not bind in significant quantities with CK-MM$_B$ or CK-MM$_C$ isoforms. Similarly, the term "anti-(CK-MM$_B$)antibody" is defined herein to designate an antibody which binds selectively with CK-MM$_B$ and which does not bind in significant quantities with CK-MM$_A$ or CK-MM$_C$ isoforms, and the term "anti-(CK-MM$_C$) antibody" is defined herein to designate an antibody which binds selectively with CK-MM$_C$ and which does not bind in significant quantities with CK-MM$_A$ or CK-MM$_B$ isoforms. The term "anti-(CK-MM$_{A+B}$) antibody" is defined herein to designate an antibody which binds selectively with CK-MM$_A$ and CK-MM$_B$ and which does not bind in significant quantities with or CK-MM$_C$ isoforms. Anti-(CK-MM$_{A+B}$) can comprise a monoclonal antibody, or a mixture of anti-(CK-MM$_A$) antibodies and anti-(CK-MM$_B$) antibodies.

CK-MB$_A$ (the tissue-specific isoform of CK-MB, also known as CK-MB$_2$) is a transiently elevated substance released during a myocardial infarction and is endogenously altered to the CK-MB$_B$ isoform (also known as CK-MB$_1$). Commercially available antibodies (available, for example, from International Immunoassay Laboratories, Inc. and Boehringer Manheim) specific for CK-BB bind with both isoforms and measure total CK-MB (CK-MB$_{A+B}$). Commercially available antibodies (available, for example, from International Immunoassay Laboratories, Inc. and Boehringer Manheim) specific for CK-MM also bind with both isoforms and measure total CK-MB (CK-MB$_{A+B}$). A novel antibody of this invention designated anti-(CK-MB$_B$) preferentially binds the CK-MB$_B$ isoform and does not bind in significant quantities with CK-MB$_A$. A preferred CK-MB$_B$ antibody is a monoclonal antibody produced by HB9914. The preferred CK-MB$_B$ antibody is also an anti-(CK-MM$_C$) antibody.

MI-P$_A$ is a proteinaceous substance believed to have a molecular weight of approximately 70,000, which is released at the time of, and is indicative of the occurrence of, a myocardial infarction. MI-P$_A$ has been tentatively identified as cytoplasmic malate dehydrogenase. It preferentially binds to the novel anti-(MI-P$_A$) antibody of this invention.

MI-D$_B$ is a proteinaceous substance having a molecular weight of approximately 55,000. It is believed to be derived from a transiently elevated substance, MI-D$_A$, released at the time of a myocardial infarction. MI-D$_B$ binds preferentially with the novel anti-(MI-D$_B$) antibody of this invention.

One aspect of the method herein is a test used for diagnosis of an acute disease event, such as a myocardial infarction. Evaluation of the calculated ratio of two immunologically measured analyte sets provides an estimate of the elapsed time since the occurrence of the myocardial infarction, and provides the medical practitioner with information on preferred courses of treatment. For example, tPA (tissue plasminogen activator) treatment is optimally effective if closely timed to the occurrence of an acute myocardial infarction. Decreased effectiveness of tPA treatment, and the high cost of such treatment, can militate against its use if substantial time has elapsed since acute myocardial infarction. The use of the method herein provides a simple, effective method for estimating the elapsed time since the onset of the acute myocardial infarction.

In accordance with the method herein, a sample is immunologically assayed to determine the concentration of each of a first and second analyte set. Each analyte set independently comprises at least one member selected from the group consisting of a transiently elevated substance, its endogenously altered forms, and combinations thereof. The first and second analyte sets are not the same. The rate of conversion of transiently elevated substances will vary according to the substances being assayed, and the endogenous conversion factors which affect them. The ratio of the first and second analyte sets is determined, and provides a numeral which is compared to a standard curve, yielding an estimate of the lapsed time since the acute incident. The specific standard curve will vary according to the acute event, the analytes assayed, and the reagents used. Production of such standard curves are within the skill of the art in light of the teachings herein.

According to the methods of the prior art, the absolute concentration of a specific analyte or analyte family which is indicative of an acute disease event is measured. In those patients where the acute disease process conform to the ideal, reliable data is obtained. However, some individuals consistently have significantly increased or reduced levels of the assayed substance. A patient having reduced CK-MM levels as an individual norm may have a substantial increase in CK-MM levels, indicative of a severe acute myocardial infarction, and still have CK-MM levels which fall within "normal" standards for the population at large. The assay method described herein provides a comparison of the increased presence of a substance indicative of an acute disease event with the continued presence of products present by the conversion of such substances in the individual. The use of the assay methods and procedures herein provides an individualized indication of the relative concentration of the assayed substance, rather than merely the absolute concentration of such substances.

The assay herein provides for immunological measurement of each of a first and second analyte set. Each set consists of a transiently elevated substance and/or at least one derivative product. The first and second transiently elevated substances can be different, or they can be the same. However, the first and second analyte sets cannot be the same.

A preferred embodiment of the method herein assays for the presence of a first analyte, which comprises a first transiently elevated substance, and a second analyte, which comprises an endogenously altered form of a second transiently elevated substance. In an especially preferred embodiment, the first analyte is MI-P$_A$ and the second analyte is MI-D$_B$.

The first analyte can comprise a transiently elevated substance, and the second analyte comprises the first analyte and at least one of its endogenously altered forms. Exemplary of such an assay is an assay to determine CK-MM$_A$ as the first analyte, and CK-MM$_{A+B}$ as the second analyte. In another embodiment, the first analyte set can be a transiently elevated substance and its endogenously altered form and the second analyte can be the endogenously altered form. Exemplary of such an assay is CK-MB$_{A+B}$ as the first analyte and CK-MB$_B$ as the second analyte. Alternatively, the first analyte can comprise a transiently elevated substance, and the second analyte is an endogenously altered form of the substance. Exemplary of such an assay is an assay to determine CK-MM$_A$ as the first analyte and CK-MM$_C$ as the second analyte.

It will be understood that while the two analyte sets are designated as "first" and "second" analyte sets, such designation is for clarity of reference only. The sets may be assayed in any convenient order.

It will be also apparent to one skilled in the art that it is not mandatory that a transiently elevated substance be measured for all assay systems. It may be desired to provide an assay in which both the first and second sets comprise endogenously altered forms of a transiently elevated substance released at onset of acute incident, wherein first and second sets are not the same. Two assays which are exemplary of such a method are the measurement of CK-MM$_B$ as the first analyte and CK-MM$_C$ as the second analyte, or measurement of CK-MM$_B$ as the first analyte and CK-MM$_{B+C}$ as the second analyte.

The method of this invention can use monoclonal antibodies, polyclonal antibodies, affinity purified antibodies, or mixtures thereof which exhibit sufficient CK-binding specificity. Generally, monoclonal antibodies and mixtures of monoclonal antibodies are preferred. Reagent antibodies and kits containing them are also aspects of the invention herein.

The assay method herein for determining the lapse of time since an acute biological incident comprises (a) determining the serum concentration of each of a first analyte set and a second analyte set, each set being selected from the group consisting of a transiently elevated substance, its endogenously altered forms, and combinations thereof, wherein the first and second analyte sets are not the same; and (b) determining the ratio of the first and second analyte sets. The ratio of first and second analyte sets provides an indication of the lapse of time since the acute incident. Preferably the first and second analyte sets are selected from the group consisting of MI-P$_A$, MI-D$_B$, total CK-MM, CK-MM$_A$, CK-MM$_B$, CK-MM$_C$, total CK-MB, CK-MB$_B$ and combinations thereof.

It is also an aspect of the invention herein to use the anti-(MI-D$_B$) antibody reagents of this invention to determine the concentration of MI-D$_B$ in serum or plasma, and thus to diagnose the occurrence of acute myocardial infarction. MI-D$_B$ is a transiently elevated protein which is not normally present in serum, or which is normally present in such small quantities as to be effectively absent. MI-D$_B$ provides an indication of acute myocardial infarction which is more sensitive and accurate than any indicator presently available.

The method herein for determining the lapse of time since an acute biological episode comprises determining the concentration of a first analyte set selected from the group consisting of a transiently elevated protein, its endogenously altered forms, and combinations thereof; determining the concentration of a second analyte set selected from the group consisting of a transiently elevated protein, its endogenously altered forms, and combinations thereof, wherein the first and second analyte sets are not the same; and determining the ratio of the first and second analyte sets.

One specific embodiment of this invention includes a step of contacting an anti-(MI-D$_B$) antibody with patient plasma or serum to effect binding of MI-D$_B$ in the sample with the antibody. In the sandwich immunoassays of this invention, reagent MI-D$_B$ protein or anti-(MI-D$_B$) antibody is insolubilized by binding directly or indirectly with a suitable insoluble support. Competition assays to determine MI-D$_B$ in a sample can be used. Immunological measurement of MI-D$_B$ provides a sensitive indication of the occurrence of an acute myocardial infarction. When combined with a determination of a derivative substance and a calculation of the ratio of the MI-D and the derivative substance, such measurements can provide an indication of the lapse of time since the occurrence of the myocardial infarction. In one embodiment, CK-MM and CK-MM$_C$ in a sample are each determined. In a preferred embodiment, MI-P$_A$ and MI-D$_B$ in a sample are determined. In another preferred embodiment, total CK-MB and CK-MB$_B$ are determined.

An alternate embodiment of this invention includes a step of contacting an anti-(CK-MM$_A$) antibody with patient serum or, preferably plasma, to effect binding of CK-MM$_A$ in the sample with the antibody. Another aspect of the method of this invention includes a step of contacting an anti-(CK-MM$_{A+B}$) antibody or a mixture of anti-(CK-MM$_A$) antibody and anti-(CK-MM$_B$) antibody with the patient sample to effect binding of CK-MM$_A$ and CK-MM$_B$ in the sample with the antibodies.

Antibodies to CK-MM can be used in combination with specific anti-(CK-MM isoform) antibodies in an assay herein. Antibodies to CK-MB can be used in combination with anti-(CK-MB$_B$) antibodies in a similar manner to quantitate CK-MB$_B$, CK-MB$_{A+B}$. In one such sandwich immunoassay for CK-MM isoforms, CK-MM isoforms are bound by anti-(CK-MM) antibody. An antibody to a specific CK-MM isoform is used to determine the specific isoform bound to the anti-(CK-MM) antibody. For example, an anti-(CK-MM) antibody is bound to an insoluble support, and the CK-MM isoforms in the sample are insolubilized by contacting the bound antibodies with the sample for a time sufficient to permit antibody-antigen binding. The CK-MM analyte on the insoluble support is then selectively bound with labeled anti-(CK-MM isoform) antibody, or a mixture of labeled anti-(CK-MM isoform) antibodies, to determine the isoform or isoforms of interest. This embodiment comprises (a) contacting the sample or an aqueous dilution thereof with an insoluble support to which anti-(CK-MM) antibody is bound for a time sufficient to permit binding between the antibody and CK-MM compounds in the solution, and removing the aqueous solution; (b) contacting the insoluble support with a solution of a labeled anti-(CK-MM isoform) antibody for a time sufficient to permit antibody binding with CK-MM isoform or isoforms bound to the insoluble support, and removing the solution from the support; and (c) determining the labeled antibody bound to the insoluble support.

In an alternate sandwich assay for CK-MM isoforms, the selectively binding antibody, i.e., anti-(CK-MM$_A$)

antibody or other anti-(CK-MM isoform) antibody, is bound to the insoluble support. The specifically binding CK-MM isoform analyte is insolubilized by contacting the sample with the antibody-covered insoluble support. The analyte bound to the insoluble support can be determined by binding with a labeled anti-(CK-MM) antibody. The labeled anti-(CK-MM) antibody embodiment comprises (a) contacting the sample or an aqueous dilution thereof with an insoluble support to which anti-(CK-MM isoform) antibody is bound for a time sufficient to permit binding between the antibody and the CK-MM isoform or isoforms in the solution, and removing the aqueous solution; (b) contacting the insoluble support with a solution of labeled anti-(CK-MM) antibody for a time sufficient to permit antibody binding with CK-MM isoform or isoforms bound to the insoluble support, and removing the solution from the support; and (c) determining the labeled antibody bound to the insoluble support.

In yet another embodiment of the assay herein, specific anti-(CK-MM isoform) antibodies act both as the capture antibody and as the labeling antibody. Such an assay comprises (a) contacting the sample or an aqueous dilution thereof with an insoluble support to which anti-(CK-MM isoform) antibody is bound for a time sufficient to permit binding between the antibody and the CK-MM isoform or isoforms in the solution, and removing the aqueous solution; (b) contacting the insoluble support with a solution of labeled anti-(CK-MM isoform) antibody for a time sufficient to permit antibody binding with CK-MM isoform or isoforms bound to the insoluble support, and removing the solution from the support; and (c) determining the labeled antibody bound to the insoluble support.

If the analyte has enzyme activity, the activity of the material bound to the insoluble support can be determined. In such an enzyme activity measurement embodiment, the insoluble support is contacted with a substrate or other material which, in the presence of the enzyme, yields a physically detectable product such as a chromophore.

In a competition immunoassay of this invention, the selectively binding antibody, especially anti-(MI-$P_A$) antibody, anti-(MI-$D_B$) antibody, anti-(CK-MM) antibody, or one or more anti-(CK-MM isoform) antibody are bound to the insoluble support. In one embodiment, the insoluble support is contacted with a mixture of the sample and labeled reagent analyte for which the sample is being assayed, and the labeled material remaining in the solution or bound to the insoluble support is measured. This embodiment comprises (a) contacting a mixture of sample and a predetermined amount of labeled reagent analyte with an insoluble support to which the anti-(analyte) antibody is bound, for a time sufficient to permit binding between the antibody and analyte, and separating the insoluble support from the liquid phase; and (b) determining the amount of labeled analyte present on the insoluble support or remaining in the liquid phase.

In another embodiment, an insoluble support to which the analyte being assayed is adhered is contacted with a mixture of the sample and labeled anti-(analyte) antibody corresponding to the specific transiently elevated substance or derivative substance analyte being assayed, and the labeled material remaining in the solution or bound to the insoluble support is measured. This embodiment comprises (a) contacting a mixture of sample and a predetermined amount of labeled anti-(analyte) antibody with an insoluble support to which reagent CK-MM isoform is bound, for a time sufficient to permit binding between the antibody and analyte, and separating the insoluble support from the liquid phase; and (b) determining the amount of labeled anti-(analyte) antibody present on the insoluble support or remaining in the liquid phase.

In the above methods, the insoluble supports with the reagent analyte or antibody bound thereto are important aspects of this invention.

Suitable incubation times for binding of anti-(MI-P) antibodies, anti-(MI-D) antibodies, anti-(CK-MB) antibodies, anti-(CK-$MB_B$) antibodies, anti-(CK-MM) antibodies, and anti-(CK-MM isoform) antibodies with their respective protein binding partners are from 1 to 240 minutes at temperatures within the range of from 16° to 40° C., the preferred contact time being at least 15 minutes at temperatures within the range of from 20° to 26° C.

A wide variety of compounds can be employed as the solid support, the primary consideration being the binding of the antibody or protein to the surface, the absence of interference with the reaction of the label and reagents used to develop it, and the absence of interference with the examination of the developed label. In particular, if fluorescence or chromogenic spectrum is being measured, the insoluble support should not provide interference.

Organic and inorganic polymers, both natural and synthetic, can be employed as the solid support. Examples of suitable polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, styrene-acrylonitrile copolymers, rayon, nylon, polyvinylbutyrate, polyformaldehyde, etc. Other materials which can be employed as the insoluble support are silica gel, silicon wafers, glass, paper, insoluble protein, metals, metalloids, metal oxides, magnetic materials, semi-conductive materials, cements or the like. In addition are included substances that form gels, i.e., proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12-24 carbon atoms) alkyl ammonium salts and the like.

A preferred diagnostic support of this invention comprises polystyrene, styrene copolymers including styrene-(vinyl monomer) copolymers such as styrene-acrylonitrile copolymers, polyolefins such as polyethylene and polypropylene, and acrylate and methacrylate polymers and copolymers.

An especially preferred support comprises magnetizable materials in particulate form. Traditional interference by such magnetizable solid supports may be minimized by adding magnetizable particles to each of the reaction steps. Magnetic interference produced at each step may be made nearly equal, and thus is effectively cancelled. Magnetizable particles may be easily separated from the serum or other solution by application of a magnet to concentrate the particles.

The antibody can be bound to the support by any method of bonding which does not significantly reduce the antibody binding sites and which binds sufficiently to permit separation of the insoluble support from the liquids and rinse solutions without significant detachment of antibody from the surface of the support. Non-covalent bonding can be achieved by adsorption, ionic bonding, van der Waals adsorption, electrostatic bonding, and other non-covalent bonding. The antibody can also be bound to the support by covalent bonding. A particularly advantageous support for this procedure comprises a microtiter plate having a plurality of wells. The well surface, or nitrocellulose or plastic cup inserts of other material therein can constitute the antibody support.

In a procedure for non-covalent adhesion of antibody to the surface of an insoluble support, the antibody material can be applied to the surface of a support such as a polystyrene microtiter well or polystyrene individual insert well therefor, in an aqueous buffer solution. The surface is initially cleaned with a cleaning fluid such as methanol and dried. The buffered antibody solution is placed in the well or insert cup and incubated at room temperature until adsorption occurs, for example for from 2 to 18 hours and preferably from 16–18 hours, at temperatures of from 4° to 40° C. and preferably from 20° to 26° C. The well is then rinsed with a weak saline solution and dried. Other procedures for covalently adhering antibodies to insoluble supports are described by I. Chibata in IMMOBILIZED ENZYMES, Halsted Press, New York, 1978, and by A. Cuatrecasas, *J. Bio. Chem.* 245:3059 (1970), the entire contents of which are hereby incorporated by reference. The surface can be coated with a protein and coupled with antibody using the procedures described in U.S. Pat. No. 4,210,418 using glutaraldehyde as a coupling agent, for example. In an alternate procedure, the well can be coated with a layer having free isocyanate groups such as a polyether isocyanate. Application of the antibody in aqueous solution thereto effects the requisite bonding. In another procedure, the antibody can be coupled to a hydroxylated material by means of cyanogen bromide as described in U.S. Pat. No. 3,720,760. In a still further procedure, Staphylococcus Protein A can be bound to the insoluble support, and the $F_c$ chain of the antibody can be conjugated with the Protein A.

Removal of solutions from solid surfaces is facilitated by applying a rinse solution. The rinse solutions, samples, and all process solutions in which CK-MM enzymes are present should preferably contain a chelating agent such as EDTA to stabilize the enzyme and any conversion factor which could convert it to another form. Therefore, plasma, which contains EDTA, is preferred over serum as the sample. However, keeping serum samples at 0° to 4° C. for a short period of time also prevents further conversion of the transiently elevated substance to its altered forms. A suitable rinse solution is an aqueous phosphate buffer solution having a phosphate molarity of from about 0.01 to 0.05, a pH of from 6 to 8, and containing from about 0.01 to 0.01 weight percent nonionic surfactant. Suitable nonionic surfactants include polyoxyethylene ethers (BRIJ) such as lauryl, cetyl, oleyl, stearyl, and tridecyl polyoxyethylene ethers; polyoxyethylenesorbitans (TWEEN) such as polyoxyethylenesorbitan monolaurate, monopalmitate, monostearate, monoleate and trioleates; and other polyoxyethylene ethers (TRITON), for example. A preferred nonionic surfactant is octylphenoxypolyethoxy ethanol having 40 ethylene oxide units (TRITON X-405, Rohm and Haas Company, Philadelphia, Pa.).

In embodiments using a second antibody-antigen binding, the insoluble surface is contacted with the support in the same manner as described above with regard to the first antibody-antigen binding, with the exception that the binding is conducted with a substantial excess of the second antibody.

The final step in all embodiments of this invention is the determination of the presence of an antibody or labeled CK-MM isoform, either on an insoluble material or in a solution. The manner of determining the antibody or CK-MM isoform is different for each type of labeled reagent used. Procedures for label determinations are well established in the art, for example as described by Voller et al, IMMUNOASSAYS FOR THE 80s. Baltimore: University Park Press (1981) supra.

If the target moiety to be measured is an unlabeled antibody bound to the insoluble support, the preferred manner of determining the target moiety involves contacting the insoluble support with a solution of labeled Protein A or a labeled secondary antibody which will bind with the primary antibody. Suitable antibodies include labeled secondary antibodies which bind with the Fc portion of primary antibodies.

Both monoclonal and polyclonal secondary antibodies which bind to the Fc portion of other antibodies and labeled Protein A are readily available from commercial sources. These can be distinctively labeled in the same manner as described above for labeling the primary antibodies. Suitable examples are described by Catty et al, in "Antisera in Immunoassays with Special Reference to Monoclonal Antibodies to Human Immunoglobulins", *IMMUNOASSAYS FOR THE 80's*, supra, pp 133–153 and the publications cited therein, the entire contents of which are hereby incorporated by reference.

In the preferred embodiments of this invention, the presence and amount of a labeled antibody or labeled reagent analyte is determined. Labels which can be directly observed or measured are the most easily determined, and a wide variety of manual, semiautomatic and automatic analyzers are available for increasing the efficiency of the analysis. Examples of such labels are radiolabels which can be measured with radiation counting devices; pigments, dyes or other chromogens which can be visually observed or measured with a spectrophotometer; spin labels which can be measured with a spin label analyzer; and fluorescent moieties which can be visualized under ultraviolet light or can be measured with standard fluorometers, for example. The label can be a luminescent substance such as a phosphor or fluorogen, a bioluminescent substance, a chemiluminescent substance or a metal containing substance.

Amplification and greater distinctions from background can be achieved by use of enzyme labels or enzyme labeling systems. The substrate is selected to yield the preferred measurable product. Chromogenic and fluorogenic enzymes are preferred. These are enzymes for which substrates yielding chromogen and fluorogens, respectively, are known.

A preferred chromogenic substrate and an enzyme uses oxidoreductases such as horseradish peroxidase and a substrate such as diaminobenzidine which yields a distinguishing color. Any other enzyme-chromogen yielding substrate combination can be used if it provides distinguishing pigmentation.

Enzyme combinations with fluorogen substrates which can be used are described in U.S. Pat. No. 4,190,496, for example, the contents of which are hereby incorporated by reference. The preferred fluorogenic enzymes and suitable substrates corresponding thereto include horseradish peroxidase for which a suitable substrate is homovanillic acid or 4-hydroxy-3-methoxyphenylacetic acid, beta-galactosidase for which a suitable substrate is 4-methylumbelliferyl-beta-D-galactoside, alkaline phosphatase for which a suitable substrate is 4-methylumbelliferyl phosphate, other umbelliferyl phosphates such as 4-carboxyum-bellifery phosphate, and umbelliferyl phosphate 4-carboxy alkylesters, etc.

To develop the chromogen or fluorogen, the insoluble support is contacted with an aqueous solution of the substrate containing from $10^{-2}$ to $10^{-10}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for a sufficient time for the fluorescent reaction product to form. At temperatures of from 18° to 40° C., incubation times of from 5 to 240 minutes can be used. Preferably, the temperature is within the range of from 20° to 26° C., and the incubation time is from 30 to 90 minutes.

For further amplification, an immunoperoxidase method using biotin-avidin complexes can be used. This procedure uses a biotin labeled antibody. The biotin is covalently bonded to the secondary antibody by conventional procedures such as those described above for binding enzymes to the primary antibody with a large molar excess of biotin to antibody, preferably with a molar ratio of at least 100:1 biotin to antibody.

A preferred biotin-avidin complex includes avidin and a biotinylated enzyme. The enzyme can be one of the enzymes previously described. Avidin-biotin systems using immunoperoxidase techniques are described by Hsu et al, in *J. Histochem. Cytochem.* 29(4):577–580 (1981), *Am. J. Clin. Path.* 75(5):734–738 (1981), and *Am. J. Clin. Path.* 75(6):816–821 (1981). Systems applying avidin-biotin systems are also commercially available from Vector Laboratories, Inc. of Burlingame, Calif., and are described in their customer literature.

In one system, the rinsed support to which biotin labeled antibody is bound is contacted with an avidin-(labeled biotin) complex. The preferred avidin-biotin complex is prepared by mixing a large molar excess of avidin with the biotinylated enzyme. Such a complex is VECTASTAIN ABC, from Vector Laboratories, Burlingame, Calif. The biotin can also be labeled with other conventional labels such as a luminescent substance, e.g., a phosphor or fluorogen, a bioluminescent substance, a chemiluminescent substance, a radioactive substance, or an enzyme, chromophor, pigment, spin label, or metal containing substance. These labels are covalently bonded to the biotin by conventional procedures appropriate to the chemical groups on the label and which have been described above for applying the same labels to antibody reagents.

The avidin-biotin complex is applied to the insoluble support in a suitable aqueous buffer solution such as the PBS solutions described above for applying antibodies to the insoluble support. The complex solution is applied for a time sufficient to permit binding of the avidin-biotin complex with the biotin which is present on the support, if any. Following this step, the excess avidin-biotin complex solution is removed, and the insoluble support is preferably rinsed with a suitable rinse solution such as the rinse solution described above, for example.

The insoluble support is then examined by procedures appropriate for the particular avidin-biotin complex label employed. These procedures are conventional. For example, if a radioactive label is employed, the insoluble support can be examined with a Geiger counter to measure the level of residual radioactivity on the insoluble support. Alternatively, if the label is a phosphor or a fluorogen, it can be examined under a fluorescent microscope. If the label is a chromophor or a pigment, the insoluble support can be examined under a microscope using ordinary light.

In embodiments wherein the last step is the measurement of enzymatic activity of MI-P, MI-D or CK-MM isoforms bound to the insoluble support, the insoluble support can be contacted with an aqueous solution of a substrate which, in the presence of the MI-P, MI-D or CK-MM enzyme, will yield a physically detectable product. Suitable substrates are described in U.S. Pat. Nos. 3,994,783, 4,012,285, 4,067,775 and 4,260,678, the entire contents of these patents and the patents and other publications listed therein being hereby incorporated by reference in their entireties. In one procedure, CK specifically catalyzes the transphosphorylation of ADP (adensine diphosphate) to ATP (adenosine triphosphate). Hexokinase is used to catalyze the phosphorylation of ATP and glucose to glucose-6-phosphate. Glucose-6-phosphate is then oxidized and NAD(nicotinamide adenine dinucleotide) reduced in the presence of glucose-6-phosphate dehydrogenase (G6PD) to 6-phosphogluconate and NADH. Nitro blue tetrazoleum (NBT) is added at the end of a timed incubation. NADH reduces NBT to a colored formazan with maximum absorbence at 530 nm. 1-Methoxy phenazine methosulfate (MPMS) catalyzes formazan production. This procedure is described by Nachlas et al, *Anal. Biochem.* 1:317 (1960), and the DATA-ZYME reagents therefor are available from Data Medical Associates, Inc., 2016 East Randol Mill Road, Arlington, Tex.

The ratio of the immunologically measured first and second analyte sets is determined, and provides a numeral which is compared to a standard curve. The standard curve will vary according to the acute event, the analytes assayed, and the reagents used. The production of such standard curves are within the skill of the art in light of the teachings herein. The calculated ratio provides an estimate of the lapsed time since the acute incident. For example, the diagnosis of myocardial infarction can be determined by measurement of MI-$P_A$ in a serum or plasma sample. The ratio of MI-$P_A$ and MI-$D_B$ in the sample provides an estimate of the lapse of time since the myocardial infarction.

Alternatively, the two analyte sets can each comprise at least one of CK-$MM_A$, CK-$MM_B$ and CK-$MM_C$. The two analyte sets cannot be the same. For example, the first analyte set may comprise CK-$MM_C$, and the second analyte set may comprise total CK-MM, or alternate CK-MM subforms. The time of the infarction can be accurately estimated based upon the measurements. For example, if the patient has had a recent AMI, the ratio total CK-MM:CK-$MM_C$ will be relatively large, as endogenous conversion factors will not have converted the large CK-$MM_A$ influx to CK-$MM_B$ and CK-$MM_C$.

If the patient has not had a recent AMI, the ratio of total CK-MM:CK-MM$_C$ will reflect normal endogenous conversion rates.

Generally, there are two types of antibody reagents which find use herein. One type binds with specific isoform of either a transiently elevated substance or its derivative product, i.e., anti-(MI-P$_A$), anti-(MI-D$_B$), anti-(CK-MM$_A$), anti-(CK-MM$_B$), or anti-(CK-MM$_C$). The second type binds preferentially with two or more separate isoforms of the family of substances, i.e., anti-(CK-MM$_{A+B}$), which binds preferentially with both CK-MM$_A$ and CK-MM$_B$, but does not bind significantly with CK-MM$_C$ or CK-MB. Antibodies can be polyclonal or monoclonal.

Polyclonal antibodies can be prepared by conventional procedures, with any mammal used for polyclonal antibody production. Generally a rabbit, guinea pig or goat is adequate. In producing the antibody, a predetermined amount of antigen is diluted with a physiological saline solution in a suitable concentration. This diluted solution is further diluted by mixing it with a complete Freund's adjuvant to prepare an emulsion. The suspension is then administered to the mammal. For example, the suspension can be administered by intraperitoneal, intramuscular or subcutaneous routes to a rabbit in an amount of 0.05 to a maximum, non-lethal dose which might be as high as 5 mg of the antigen in every administration, and the administration can be continued every other week for 2 to 10 months. Blood is removed from the mammal when the antibody titer is sufficiently elevated, generally one to 2 weeks after the last challenge administration of the suspension. The blood taken from the animal is treated by centrifugal separation to separate the serum containing the antibody.

The polyclonal antibody serum is then affinity purified using conventional affinity chromatography techniques such as those described by Mishell and Shilgi in SELECTED METHODS IN CELLULAR IMMUNOLOGY. San Francisco: Freeman (1980), the entire contents of which are hereby incorporated by reference. Suitable absorbents for use in affinity chromatography include cross-linked agarose and cross-linked polyacrylamides to which the selected antigen-binding antibody is covalently bonded. Repetition of the column separation procedures may be required to effect the desired separations.

In these procedures, the antibody solution can be applied to the column in a phosphate buffered saline solution, and the antibodies can be eluted with a 2.5 M NaSCN solution, pH 8.0. Antibody concentration, if desired, can be achieved by negative pressure dialysis or ultrafiltration. The antibody solution is stable at temperature of 4° C. or less.

Monoclonal antibodies of this invention are prepared by conventional procedures, generally following the method of Kohler and Milstein, *Nature* 256:495–497 (1975). More recent applicable procedures are reviewed in Goding, MONOCLONAL ANTIBODIES: PRINCIPLES AND PRACTICE. New York: Academic Press (1983) and the references cited therein, the entire contents of which are hereby incorporated by reference.

A hybridoma can be prepared by immunizing mice or rats with an appropriate antigenic substance. While female A/J mice (H-2a haplotype, Jackson Laboratories, Bar Harbor, Me.) are preferred, it is contemplated that other mice or rat strains can be used. The immunization schedule and concentration of antigen in the suspension should be such as to produce useful quantities of Suitably primed splenocytes and/or lymphocytes.

The suspended spleen cells are fused with mouse or rat myeloma cells from a suitable cell line by the use of a suitable fusion promoter. While the preferred fusion promoter is polyethylene glycol (PEG) having an average molecular weight from about 1000 to 4000 (commercially available as PEG 1000, etc.), other fusion promoters known in the art, such as Sendai Virus or an electrical field, can be used. The fused cells are then appropriately cultured.

Many mouse myeloma cell lines are known and available, e.g. from members of the academic community and various deposit banks such as the American Type Culture Collection, Rockville, Md. Balb/C myeloma cells lines are preferred. The myeloma cell line used should preferably be medium sensitive so that unfused myeloma cells will not survive in a selective medium, while hybrids will survive. The most common class is 8-azaguanine resistant cell lines, which lack the enzyme hypoxanthine guanine phosphoribosyl transferase and hence will not be supported by HAT (hypoxanthine, aminopterin, and thymidine) medium. It is also generally preferred that the myeloma cell line used be of the so-called "non-secreting" type, in that it does not produce any antibody, although secreting types may be used.

The supernatant in each container or well containing a hybridoma is examined for the presence of antibody which binds selectively with the analyte of interest and which does not bind to undesired substances. Procedures suitable for screening are described by Goding (supra, pp 72–84). One suitable method involves a competition between an anti-mouse immunoglobulin bound to an insoluble support (such as a microtiter tray well) and a mixture of labeled antigen and culture supernatant. An alternate method involves a competition between an insolubilized anti-mouse immunoglobulin and a mixture of labeled antigen and culture supernatant. The amount of label bound to the insoluble support is ascertained to determine the binding of analyte in the supernatant with the antibodies in the culture supernatant. Another suitable procedure comprises the application of the culture supernatant in a dot to a layer of nitrocellulose gel to which the selected isoform is adhered, rinsing the gel layer, contacting the gel layer with a chromogen labeled antibody or fluorescent labeled antibody which will bind to the Fc portion of any antibodies bound to the gel layer, rinsing the gel layer to remove unbound labeled antibody, and examining the gel layer to determine if bound chromogen or fluorogen is evident where the dot was applied. Automatic tray readers can be used to quickly identify the wells having hybridomas yielding antibodies which bind to the proteins adhered to the insoluble surface.

The production of hybridomas yielding antibodies useful herein has been described. Specific mouse hybridomas secreting novel antibodies of this invention have been deposited with the American Type Culture Collection (ATCC), 12301 Parklawn Drive, Rockland, Md. 20856 USA, as follows: a mouse hybridoma producing anti-(MI-P$_A$) antibodies was deposited on Nov. 17, 1988 and given accession number HB9913, a mouse hybridoma producing anti-(MI-D$_B$) antibodies was deposited on Nov. 17, 1988 and given accession number HB9912, a mouse hybridoma producing anti-(CK- MM$_C$) antibodies was deposited on Nov. 17, 1988 and given accession number HB9914.

After a desired hybridoma has been selected and cloned, the resultant antibody can be produced by in vitro culturing in a suitable medium followed by recovery of the antibody from the supernatant. Alternatively, the hybridoma can be injected into mice, preferably syngenic or semisyngenic mice. The hybridoma will cause formation of antibody producing tumors after a suitable incubation time. These will produce a high concentration of the desired antibody (about 5-20 mg/ml) in the bloodstream and peritoneal exudate (ascites) of the host mouse. Although the host mice will also have normal antibodies in their blood and ascites, the concentration of the normal antibodies will be only about 5 percent of the concentration of the desired monoclonal antibody.

The antibodies and antigens of this invention can be coupled with a variety of moieties useful for diagnostic methods. In general, procedures suitable for binding such diagnostic labeling moieties to antibodies can also be used for binding the moieties to the antigen for immunodiagnostic purposes.

In several embodiments of the diagnostic method of this invention, a labeled antibody reagent is used. The antibody reagent is labeled, i.e., chemically bonded to a distinctive moiety which can be observed or measured to verify or quantify the presence of the antibody in a solution or on a solid surface. Ligands and groups which can be bound to the antibodies of this invention for use in diagnostic procedures include elements, compounds or biological materials which have physical or chemical characteristics which can be used to distinguish the antibodies to which they are bonded from other antibodies.

The specific activity of the radiolabels used with radio-labeled antibodies of this invention antibody depends upon the half-life and isotopic purity of the radioactive label, and how the radiolabel is incorporated into the antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---|---|---|
| $^{14}C$ | $6.25 \times 10^1$ | 5720 years |
| $^3H$ | $2.91 \times 10^4$ | 12.5 years |
| $^{35}S$ | $1.5 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes such as those listed in Table A are generally known in the art. Tritium labeling procedures are described in U.S. Pat. No. 4,302,438, for example. Iodinating, tritium labeling and $^{35}S$ labeling procedures especially adapted for murine monoclonal antibodies are described by Goding, MONOCLONAL ANTIBODIES: PRINCIPLES AND PRACTICE. New York: Academic Press pp 124-126 (1983) and the references cited therein. Other procedures for iodinating antibodies are described by Hunter and Greenwood, *Nature.* 144:945 (1962) and David et al, *Biochemistry* 13:1014-1021 (1974) and in U.S. Pat. Nos. 3,867,517 and 4,376,110.

Antibodies labeled with enzymes are particularly useful. Suitable procedures for enzyme labeling of antibodies are described in U.S. Pat. Nos. 3,654,090, 4,214,048, 4,289,747, 4,302,438, 4,312,943, 4,376,110, and Re. No. 31,006, and the references cited therein, for example. Examples of other suitable systems are described by Pesce et al, *Clin. Chem.* 20(3):353-359 (1974) and Wisdom, *Clin. Chem.* 22:1243 (1976). Table B demonstrates suitable enzyme classes, and provides specific examples for each class:

TABLE B

| Class | Enzyme Example |
|---|---|
| Hydrolases Carbohydroases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Demolases | Aldolase |
| Oxidases | Glucose oxidase |
| | Horseradish peroxidase |
| Other enzymes | Beta-galactosidase |
| | Phosphatases |
| | Phosphorylases |
| | Hexokinases |

These and other suitable enzymes are described in Hawk, et al, PRACTICAL PHYSIOLOGICAL CHEMISTRY, New York: McGraw-Hill pp 306-397 (1954).

Fluorogenic enzymes (enzymes in the presence of which a selected substrate will produce a fluorescent product) are also highly useful labeling moieties. Methods for selectively conjugating enzymes to antibodies without impairing the ability of the antibody to bind with antigen are well known in the art. Suitable enzymes and procedures for coupling them to antibodies are described by Wilson et al, "Recent developments in the periodate method for conjugating horseradish peroxidase (HRPO) to antibodies." INTERNATIONAL CONFERENCE IN IMMUNOFLUORESCENCE AND RELATED STAINING TECHNIQUES. W. Knapp et al, editors. Amsterdam: Elsevier pp 215-244 (1978); Sullivan et al, "Enzyme immunoassay: a review." *Annals of Clinical Biochemistry* 16:221-240 (1979); and in U.S. Pat. No. 4,190,496, for example. Preferred fluorogenic enzymes and suitable substrates corresponding thereto include horseradish peroxidase for which a suitable substrate is homovanillic acid or 4-hydroxy-3-methoxy-phenylacetic acid; beta-galactosidase, for which a suitable substrate is 4-methylumbelliferylbeta-D-galactoside; and alkaline phosphatase, for which a suitable substrate is 4-methylumbelliferyl phosphate and other umbelliferyl phosphates such as 4-carboxyumbelliferyl phosphate and umbelliferyl phosphate 4-carboxyalkyl esters, etc.

Examples of suitable procedures for enzyme labeling of the antibody include the use of carbodiimides, dialdehydes, and bifunctional coupling reagents. Linkage of enzymes through amide groups can be achieved by treating the proteins with thionyl chloride, N-hydroxysuccinimide or similar reagents in an anhydrous solvent such as dimethylformamide, dioxane, dimethylsulfoxide, tetrahydrofuran and the like. Alternative coupling agents include carbodiimides such as 1-ethyl-3-(3-N,N'-dimethylamino-propyl)carbodiimide or 1-cyclohexyl-3-(2-morpholinoethyl)carbodiimide methyl-p-toluenesulfonate.

The carbohydrate moiety of an enzyme can also be oxidized to an aldehyde and reacted with lysyl amino groups of immunoglobulins to form a Schiffs base. Reduction with sodium borohydride effects a stable linkage of enzyme and antibody. Horseradish peroxidase with antibody can be efficiently linked to immunoglobulins by the method of Wilson, supra.

Fluorescent labeled antibodies can be prepared from standard fluorescent moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers are described by Stryer, Science 162:526 (1968) and Brand et al, "Fluorescent probes for structure," *Annual Review of Biochemistry* 41:843–868 (1972). The anti-ADP antibodies of this invention can be labeled with fluorescent groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamine group derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescamine and fluorescein isothiocyanate are readily available.

Another group of fluorescent compounds are the naphthylamines, having an amino group in the alpha or beta position. Included among the naphthylamino compounds are 1-dimethylaminonaphthyl-5-sulfonate, 1-anilino-8-naphthalene sulfonate and 2-a-toluidinyl-6-naphthalene sulfonate. Other dyes include 3-phenyl-7-isocyanatocoumarin; acridines such as 9-isothiocyanatoacridine and acridine orange; N-[p-(2-benzoxazolyl)phenyl]maleimide; benzoxadiozoles such as 4-chloro-7-nitrobenzo-2-oxa-1,3-diazole and 7-(p-methoxybenzylamino)-4-nitrobenzo-2-oxa-1,3-diazole; stilbenes such as 4-dimethylamino-4'-isothiocyanatostilbene and 4-dimethylanimo-4'-maleimidostilbene; N,N'-dioctadecycloxacarboxyamine-p-toluenesulfonate; pyrenes such as 8-hydroxy-1,3,6-pyrenetrisulfonic acid, 1-pyrenebutyric acid, merocyanine 540, rose bengal, 2,4-diphenyl-3(2H)-furanone, o-phthaldehyde, as well as other readily available fluorescing molecules. These dyes either have active functionalities or such functionalities can be readily introduced.

For example, antibodies can be labeled with fluorochromes by the procedures described by Goding, MONOCLONAL ANTIBODIES: PRINCIPLES AND PRACTICE. New York: Academic Press, pp 208–249 (1983). The concentration of fluorochrome is selected according to the table of Goding, p 229. For example, fluorescein isocyanate (1.0 mg/ml) or rhodamine isocyanate (10.0 mg/ml) in DMSO (dimethylsulfoxide) is prepared, and the desired volume (1–10% of total protein solution volume) is added to the protein solution dropwise, with stirring. The reaction proceeds for two hours, shielded from light. The product is purified by gel filtration on SEPHADEX G-25 gel in PBS containing 0.1% $NaN_3$ to separate the unreacted or hydrolyzed fluorochrome. The absorbence of the conjugate is measured at 280 nm and at its peak in the visible region (495 nm for fluoresceinated antibody and 550 nm for rhodaminated antibody). The fluorochrome to protein ratio is calculated according to the procedure of Goding, supra, p 224–225. Conjugates are stored at 4° C. protected from light until use. If the antibody solution concentration is less than 1 mg/ml, BSA is added to the solution to a final concentration of 1 mg/ml.

The antibodies can be covalently bonded to avidin or biotin in one embodiment of this invention. Suitable binding procedures involve cross-linking through a bifunctional cross-linking agent. Suitable bifunctional compounds are described by Peters et al *Ann. Rev. Biochim.* 46:523 (1977). Alkyl imidates show a high degree of specificity among the functional groups presented to them by a protein. The reaction is specific for primary amino groups. Examples of suitable coupling reagents include amidoesters such as dimethylmalonimidate, azides such as the acyl azide of tartryl diazide which reacts readily with immuno groups to produce amide linkages. Aryl dihal ides (e.g., 1,5-difluoro-2,4-dinitrobenzene, or 4,4'-difluoro-3,3'-dinitrophenyl sulfone, glutaraldehyde, 1-ethyl-3-(3-dimethyl aminopropyl)carbodiimide hydrochloride, dimaleimide, mixed anhydride, m-maleamidobenzoyl N-hydroxysucciinimide ester, and other known cross-linking agents.

The foregoing reagents provide essentially irreversible bonds. Bifunctional agents with functional groups such as disulfide or glycol may be used. These provide bonds which can be broken after the cross-linking reaction, if desired. Such reagents include dimethyl 3,3'-dithiobispropionimidate, succinimidyl propionimidate, N-(3-fluoro-4,6-dinitrophenyl)-cystamine, tartryl diazide, tartryl di(glycylazide) and tartryl di(epsilon-amino caproylazide).

In other instances, the bonds can be formed directly between the reagents themselves. For example, antibody can be bound to biotin through functional groups on the respective materials. As a specific example, biotin can be treated with periodate and reacted with antibody to give a Schiff base formation without inhibiting the biotin to avidin binding or blocking immunological activity of the antibody.

Known techniques using bifunctional cross-linking agents include the following: (a) a one-step glutaraldehyde linkage, Avrameas, *Immunochem.* 6:43 (1969); (b) two-step 9lutaraldehyde linkage, Avrameas, *Immunochem.* 8:1175 (1971); and (c) dimaleimide linkage, Kato et al, *Euro. J. Biochem.* 62:285 (1966).

Antibodies can be labeled with metallic radionuclides according the procedure of Hnatowich et al, *J. Appl. Rad.* 35(6):554–557 (1984) and Buckley et al, *Fed. Eur. Biochem. Soc.* 166(1):202–204 (Jan. 1984). In this procedure the antibodies are conjugated with a chelating agent such as diethylenetriaminepentaacetic acid which is capable of forming a chelate with the metallic radionuclide. A suspension of 0.1 mg/ml of the bicyclic anhydride of DTPA (diethylenetriaminepentaacetic acid) is prepared in a dry solvent such as chloroform, ether or dry DMSO. An aliquot is removed to a clean, dry tube sufficient to provide a DTPA to immunoglobulin molar ratio of 1:1 and evaporated under nitrogen. A 10–20 microliter portion of the antibody solution used (10–20 mg/ml) in 0.05M bicarbonate buffer in saline, pH 7.0-7.5 is added to the dry DTPA, and the contents are agitated for 0.5-1.0 min. The coupled protein preparation is diluted to 0.2 ml with the same buffer solution and purified on a 5 cm gel filtration column with SEPHADEX G-50 gel, using a saline eluant. The coupling efficiency is determined before purification by the addition of "chelation-grade" "In in 0.5M acetate buffer solution, pH 6.0. Thin layer chromatography is used to separate the DTPA coupled antibody for calculation of the coupling efficiency. The DTPA-coupled antibodies can be stored at 4° C. until needed for binding with metallic radionuclides.

Examples of other suitable labels are described by Voller et al, IMMUNOASSAYS FOR THE 80s. Baltimore: University Park Press (1981), and U.S. Pat. Nos. 4,220,450 and 3,960,834, the entire contents of which and the references cited therein being hereby incorporated by reference. One such example is a chemiluminescence label described by McCapra, *Quarterly Reviews* 20:485 (1966), U.S. Pat. No. 4,220,450, and Voller (supra, pp 113-125).

Labeled antigen reagents can also find use in the assays of this invention. The term "antigen" is used herein to refer to an epitope, or tissue fragment including the epitope, which binds preferentially with the assay antibody. Included are heterogeneous tissue fragments, purified homogeneous fragment compositions, and the isolated epitope, free from tissue components which are not essential for the binding properties of the epitope.

The MI-$P_A$ and MI-$D_B$ antigens can be isolated by affinity chromatography of extracts of cardiac tissue which has been extracted with neutral detergent, using anti-(MI-$P_A$) antibody or anti-(MI-$D_B$). antibody, respectively, bound to conventional affinity column materials. The treatment of the tissue extract with the column and the elution of the antigen from the column can be effected by conventional procedures. Suitable procedures for extracting and purifying proteins are described by H. Davis et al, *Canc. Res.* 46:6143-6148 (1986); V. Johnson et al, *Canc. Res.* 46:850-857 (1986); and E. Friedman et al, *Canc. Res.* 46:5189-5194 (1986); the entire contents of each of which being incorporated by reference in their entireties.

CK-$MM_A$ isoform is obtained from total CK-MM heart extract by the method of Vaidya et al, *Biochim. Biophys. Acta.* 790:230-237 (1984), which article is incorporated herein in its entirety Human heart or skeletal muscle was obtained at autopsy and preserved by freezing at −70° C. Prior to homogenization, the tissue was thawed for 2-3 h at room temperature in buffer A (50 mM Tris/100 μM EDTA/10 mM fi-mercaptoethanol (pH 7.3)). If thawing was incomplete, the tissue was left overnight at 4° C. after replenishing the buffer. Before homogenization, the tissue was minced with scissors into small pieces that were weighed and suspended in 2 ml buffer A per g tissue. Homogenization was performed in a Waring blender using three or four bursts of 15 s each at intervals of 1 min. The homogenate was centrifuged at 3000×g for 20 min, filtered through cheesecloth, and recentrifuged at 10000×g for 1 h. The pellet obtained by centrifugation was discarded and the supernatant was used for ammonium sulfate fractionation.

Salt fractionation was performed at 4° C. by adding solid ($NH_4)_2SO_4$ (Sigma, grade III) very slowly, and with constant stirring, to give a final concentration of 40% (w/v). After 1 h, the preparation was centrifuged at 10000×g for 1 h. The supernatant was further fractionated by bringing the ($NH_4)_2SO_4$ concentration to 70% (w/v). The preparation was left for 2 h or overnight at 4° C., and then centrifuged at 10000×g for 1 h. The pellet obtained was dissolved in buffer A and dialyzed against buffer A at 4° C. for 12-15 h.

The dialyzed fraction obtained by salt precipitation was loaded on a DEAE-Sepharose column (30×5 cm). A 0-325 mM NaCl gradient was passed through the column at a flow rate of 35 ml/h. Alternate fractions were analyzed for creatine kinase activity. Pools of each enzyme peak were characterized for their isoenzyme contents by agarose gel electrophoresis.

The pools of each peak characterized as creatine kinase-MM by agarose gel electrophoresis following ion-exchange chromatography were dialyzed against buffer B (50 mM Tris/300 mM glycine/10 mM β-mercaptoethanol (pH 8.6)), for 24 h at 4° C. Chromatofocusing of these creatine kinase-MM peaks was then carried out essentially following the manufacturer's instructions (Pharmacia Fine Chemicals, Sweden) except for two modifications. First, the starting buffer used was Tris-glycine instead of the Tris-acetate suggested by the manufacturer. Second, the length of the column was increased. These two modifications gave better resolution of the variants of creatine kinase-MM.

A 1.6×90 cm column was packed with Polybuffer Exchanger-94 (PBE-94) and equilibrated with buffer B. After loading the sample, creatine kinase-Mm was eluted using 7.5 mM polybuffer/acetic acid (pH 5.0). The polybuffer used was a mixture of Polybuffer-74 (70%, v/v) and Polybuffer-96 (30%, v/v), and fractions were collected at a flow rate of 50 ml/h. Creatine kinase activity of alternate fractions was assayed and the pH of every tenth fraction was measured. Each peak containing the enzyme activity was separately pooled, and concentrated with an Amicon ultrafiltration cell.

Gel filtration of the concentrated pools was performed to remove some minor contaminating proteins. The concentrated pools of creatine kinase-Mm variants were independently loaded on a 1.6×90 cm Sephacryl S-200 (Pharmacia, Sweden) column that had been pre-equilibrated with buffer A. The same buffer was used for elution and 2-ml fractions were collected at a flow rate of 15 ml/h.

CK-$MM_B$ isoform and CK-$MM_C$ isoform are obtained by the methods of Vaidya (supra) or by conversion of CK-$MM_A$ to CK-$MM_B$ and CK-$MM_C$ by the methods of Perryman et al, *Clin. Chem.* 30:662 (1984), which article is incorporated herein in its entirety.

Carboxypeptidase B (Sigma Chemical Co.) was added to purified human, canine, and rabbit tissue CK-MM in an enzyme/substrate weight ratio of 1:100 in Tris HCl buffer (pH 7.3, 25 mmol/L) and incubated at 37° C. Aliquots removed during the next hour were analyzed for CK activity by gel electrophoresis as described above. Human plasma carboxypeptidase N was added to tissue CK-MM to give concentration of 4 U/L, and aliquots were removed and analyzed as above.

In competition assay embodiments of this invention, a labeled MI-$P_A$, MI-$D_B$, CK-$MM_A$, CK-$MM_B$, CK-$MM_C$, CK-$MM_{A+B}$, CK-$MM_{A+C}$, CK-$MM_{B+C}$, and-/or CK-$MM_{A+B+C}$ is used. In general, these proteins can be conjugated with the labels described above for preparing a labeled antibody, and the covalent bonding methods for attaching the label moiety to the antibody can be the same for preparing the labeled protein. Enzyme labeled and radiolabeled reagents are particularly useful.

This invention is further illustrated by the following specific, but non-limiting examples. Temperatures are provided in degrees Centigrade and concentrations as weight percents unless otherwise indicated. Examples which are constructively reduced to practice herein are presented in the present tense, and examples which represent work which has been reduced to practice in the laboratory is presented in the past tense.

EXAMPLE 1

Preparation of Antigen

Heart tissue extract was prepared by the method of Vaidya et al, Biophys. Acta 790:230–237 (1984) or for CK-MB, by the method of Grace and Roberts, Clin. Chem. Acta 123:59–71 (1982). Fractions collected based upon peak CK activity contained relatively pure CK isoenzymes, with some contaminating proteins. Antibodies were raised against various fractions, which are generally rich in the initial forms of proteins or isoenzymes, unaltered by endogenous conversion factors. These fractions may be converted to other forms by in vitro conversion of purified fractions.

It was observed by gel electrophoresis that certain contaminating non-CK proteins remained with purified antigens. Chromatofocusing peaks 1 and 2, obtained by the method of Vaidya were used to produce monoclonal antibodies. Antibodies were produced which bind specifically to two of the contaminating proteins, MI-$P_A$, a protein with a molecular weight of approximately 70,000, and MI-$D_B$, a protein of approximately 55,000 molecular weight.

EXAMPLE 2

Preparation of Monoclonal Anti-(MI-$P_A$) Antibodies and Anti-(MI-$D_B$) Antibodies 1. Immunization protocol Eight week old female A/J mice, H-2a haplotype (Jackson Laboratories, Bar Harbor, Me.) were primed intraperitoneally with 25 μg of purified CK-MM isoform fraction according to Example 1, emulsified in complete Freund's adjuvant. 5 weeks and 8.5 weeks later, mice were boosted intravenously with 10 μg of purified fraction. Three days after the final booster immunization, the mouse was sacrificed and the spleen removed for fusion.

2. Cell fusion

Spleen cells obtained from the immunized mouse were fused with a Balb/C myeloma cell line essentially as described by Kohler and Milstein, Nature 256:495–497 (1975) using polyethylene glycol (NEN Products, Boston, Mass.) as fusion agent. The fused cells were cultured in 96-well culture plates and incubated at 37° C. in an atmosphere containing 5 vol. % $CO_2$.

3. Screening for antibodies

Culture supernatants from individual wells were screened for antibodies specific for CK-MM using solid-phase radioimmunoassay on post fusion day 8. A 100 μl (microliter) volume of culture supernatant was incubated with a volume of $^{125}$I-labeled protein obtained as fractions I, II and III by chromatofocusing (50,000 cpm) in 96 well plates (IMMULON II, Dynatech Laboratories, Alexandria, Va.) previously coated with goat anti-mouse IgG antibodies (Pal-Freeze Biologicals, Rogers, Ariz.). After 2–3 hr incubation at room temperature, the plates were rinsed 3 times with TWEEN-PBS, blotted dry and the radioactivity of the bound tracer was counted with a gamma counter.

Human heart extract was prepared by homogenizing heart tissue by the methods of Grace and Roberts, Clin. Chem. Acta 123:59–71 (1982). This material was converted by in vitro action of the endogenous conversion factors to varying states of conversion. The degree of conversion was determined by the electrophoretic method in which CK-$MM_A$, CK-$MM_B$ and CK-$MM_C$ are separated. Calibrators made from CK-MM, CK-$MM_A$ and CK-MB were also used. Antibodies which reacted with constituents of heart tissue, but measured sites not altered by the conversion factors were identified based upon their comparable reactivity to unconverted and converted heart extract. Antibodies which reacted with constituents of heart extract but measured sites altered by the conversion factors were identified based upon their differing reactivity to unconverted and converted heart extract.

4. Culture expansion and hybridoma cloning

Hybridoma culture producing antibodies specific for CK-MM, MI-$P_A$, MI-$D_B$, and CK-$MM_C$ were expanded into 24-well culture plates and 25 cm² tissue culture flasks. Cloning by limiting dilution was subsequently performed, and the cloned hybridomas secreting specific antibodies were further expanded.

5. Production of ascites

Eight week old female $CAF_1$/J mice (Jackson Laboratories, Bar Harbor, Me.) primed with incomplete Freund's adjuvant were injected intraperitoneally with $10^5$–$10^6$ hybridoma cells. Ascites were harvested 10–14 days later.

6. Purification of monoclonal antibodies

Ascites were centrifuged to remove cells and debris. An equal volume of 1,1,2-trichloro-1,2,2-trifluoroethane (Mallinckrodt, Paris, Ky.) was combined with the cell-free ascites and vigorously agitated for 10–20 min. The mixture was centrifuged to separate antibody-containing ascites from the lipid layer. The lipid-extracted ascites were heat treated (56° C., 30 min), added with 0.1% $NaN_3$, and kept at −20° C. or further purified. For further purification, ascites were precipitated with 50% saturation of ammonium sulfate, centrifuged, and the precipitates were dialyzed against 20 mM phosphate buffer, containing 15 mM NaCl, pH 7.2. For DEAE chromatography, one-step elution was carried out to obtain the IgG monoclonal antibody enriched fraction. A column was packed with DE52 (Whatman, England), was equilibrated with 20 mM phosphate buffer, 15 mM NaCl, pH 7.2, and was loaded with the dialyzed monoclonal antibody preparation at a ratio of 4 ng of protein to 1 ml of DE52 matrix. It was eluted with the same buffer, greater than 90% of the total antibody activity being eluted unbound. Nevertheless, different monoclonal antibodies appeared to behave somewhat differently with regard to the elution patterns. Therefore, a stepwise increment of salt concentration for elution is recommended.

EXAMPLE 3

Evaluating Reactivity of Monoclonal Anti-(MI-$P_A$) and Anti-(MI-$D_B$) Antibodies Changes in MI-$P_A$ and MI-$D_B$ mimic those of CK-MM isoforms.

Heart extract is prepared as described in Example 1 and is treated with carboxypeptidase as described in *Clin. Chem.* 30:662 (1984). The effect of variation in the length of carboxypepsidase treatment is shown in Table C.

Rabbit anti-($MI-P_A$) and anti-($MI-D_B$) antibodies prepared in accordance with Example 2 are each immobilized on magnetic latex particles (polystyrene particles, Seragen, Indianapolis, Ind.). Goat anti-rabbit (IgG) antibodies are passively absorbed on latex by known methods. Rabbit anti-($MI-P_A$) and anti-($MI-D_B$) antibodies are then reacted to provide solid-phase rabbit anti-($MI-P_A$) and anti-($MI-D_B$) antibodies, respectively. The suspension of this solid-phase (100 μl) is mixed with a sample of $CK-MM_A$ exposed to human serum containing conversion factors for various lengths of time at 37° C. The $^{125}I$ labeled monoclonal antibody prepared in accordance with the procedure of Example 11 is also added (100–130,000 counts per min). The immunological assay procedure is as follows:

1. Allow assay reagents to come to room temperature.
2. Label test tubes in duplicate for each calibrator, control and patient sample.
3. Pipette 25 μl of each calibrator, control and sample directly into the bottom of each tube.
4. Pipette 100 μl of $^{125}I$-labeled antibody reagent made in according to the procedure of Example 11 into the bottom of each tube.
5. Mix the solid-phase reagent consisting of immobilized rabbit anti-($MI-P_A$) antibody gently and pipette 25 μl of the suspension into each tube.
6. Shake the test tube rack to mix the contents well.
7. Incubate tubes at room temperature for 15 minutes on a rotator at 150–170 rpm.
8. Dispense 1 ml of wash buffer into all tubes.
9. Place test tubes into a magnetic rack.
10. Aspirate or decant liquid from all tubes.
11. Count all tubes in a gamma counter for one minute with the window suitably adjusted for iodine-125.
12. Calculate results. Calculate the average counts per minute (CPM) for all calibrators. Plot a calibration curve on the graph paper provided with the CPM on the y-axis and $MI-P_A$ and $MI-D_B$ concentration on the x-axis. Draw a best fitting curve. Read the concentration of each sample from the calibration curve.

The tests were compared with results obtained with electrophoretic separation of CK-MM isoforms, separated as follows. To each thawed plasma sample, 50 μl of buffer containing 200 mM EDTA, 100 mM MET (2-mercaptoethanol) in 10 mM Tris HCl buffer, pH 7.4, was added. One microliter of the sample is then applied to each well of a Corning Electro-Trace Special purpose electrophoresis film, 1% agarose (Corning, Palo Alto, Calif., Catalog #470104). Electrophoresis buffer consisted of 97% (v/v) 50 mM Tris Barbital Buffer, pH 9.15 (Gelman Scientific, Ann Arbor, Mich., High Resolution Buffer, Product #51104), and 3% (v/v) POLY-BUFFER 96 (Pharmacia, Piscataway, N.J., product #17-0714-01). Electrophoresis is carried out for 90 min at 180 volts and 4° C. Gels are then overlaid with 1 ml of Corning CARDIOTRAK-CK reagent (Corning, Catalog #470069), incubated for 37° C. for 20 min, and dried for 15 min at 60° C. Dried gels are scanned on a HELENA AUTO SCANNER and peak integration is performed manually using a HELENA QUICK QUANT III.

The results obtained are shown in Table C.

TABLE C

| Time*, Hr | Conc. Change by Electrophoresis, % | | | | | Immunological Measurement |
|---|---|---|---|---|---|---|
| | $MM_A$ | $MM_B$ | $MM_{(A+B)}$ | $MI-P_A$ | $MI-D_B$ | $MI-P_A/MI-D_B \times 100$ |
| 0 | 100 | 0 | 100 | 100 | 100 | 100 |
| 1 | 79.4 | 20.6 | 100 | 100 | 100 | 100 |
| 2 | 73.8 | 26.2 | 100 | 100 | 100 | 100 |
| 3 | 68.8 | 31.2 | 100 | 100 | 100 | 100 |
| 4 | 56.4 | 43.6 | 100 | 53 | 100 | 53 |
| 14 | 24.1 | 47.0 | 71.1 | 19 | 79 | 24 |

*Time of carboxypeptidase treatment, Clin. Chem. 30:662 (1984).

This data shows that the test based on anti-($MI-D_B$) antibody measures a substance which parallels both $CK-MM_A$ and $CK-MM_B$ in concentration. The test based on $MI-P_A$ antibody measures a substance which parallels the concentration of $CK-MM_A$. The data also shows that the ratio of the amounts of native protein to the amounts of the analyte pair decreases as the native protein remains in contact with the endogenous conversion factors.

EXAMPLE 4

$MI-P_A$ Antigen Purification

Monoclonal anti-($MI-P_A$) antibody, produced by ATCC HB9913, binding specifically with $MI-P_A$ protein obtained in accordance with the procedure of Example 2 is bound to SEPHAROSE by procedures which are conventional in the art to form an affinity column gel binding specifically to $MI-P_A$.

A column is packed with 25 ml of SEPHAROSE gel conjugated to anti-($MI-P_A$) antibody. The column is equilibrated with 2–3 volumes of buffer (0.15 M PBS, pH 7.2), and a serum solution is applied to the column. The column is then washed 10 times with volumes of PBS buffer, pH 7.2.

The flow rate of eluting buffer (sodium acetate, pH 4.0) is 15–20 ml/hr. The eluted fractions containing $MI-P_A$ antigen are collected until peak activity disappears, yielding MI-P, to which the anti-($MI-P_A$) antibody specifically binds.

The column is then washed with 10×volumes of PBS buffer, pH 7.2.

The $MI-P_A$ antigen is a protein which has a molecular weight of approximately 70,000. It has been tentatively identified as cytoplasmic or mitochondrial malate dehydrogenase.

EXAMPLE 5

$MI-D_B$ Antigen Purification

Repeating the procedures of Example 4, but replacing the anti-($MI-P_A$) antibody with anti-($MI-D_B$) antibody yields the corresponding $MI-D_B$ protein.

The $MI-D_B$ protein has a molecular weight of approximately 55,000.

EXAMPLE 6

Polyclonal Anti-($MI-P_A$) Antibodies

1. Polyclonal antiserum against $MI-P_A$ antigen, prepared in accordance with the procedure of Example 4, is elicited in rabbits using the immunization techniques and schedules described in the literature, e.g., Stollar, *Methods of Enzymology* 70:70 (1980). The antiserum is screened in a solid phase assay similar to that used for monoclonal antibodies, e.g., as described by Lange et al, *Clin. Exp. Immunol.* 25:191 (1976) and Pisetsky et al, *J. Immun. Meth.* 41:187 (1981). The initial screening criterion is binding to MI-$P_A$ antigen.

2. In the following chromatographic separation, all solutions should preferably contain a chelating agent such as EDTA to stabilize the CK-MM isoform. A column is prepared by the procedures described in AFFINITY CHROMATOGRAPH: PRINCIPLES AND METHODS. Pharmacia Fine Chemicals, AB, Box 175 S-75104 Uppsula, Sweden (1971), the entire contents of which are hereby incorporated by reference in their entirety. The column is packed with 25 ml of SEPHAROSE gel bound to MI-$P_A$ isoform as follows: Freeze-dried CNBr-SEPHAROSE 4B powder (Pharmacia) is swelled for 15 min in 1 mM HCl. The gel is washed on a sintered glass filter (porosity G-3) with a total of 200 ml of I mM HCl per gram of gel (dry wt.) This is done in several aliquots, the supernatant being suctioned off between successive additions. 5 mg of MI-$P_A$, prepared according to the procedures of Example 4, for each 1 ml of gel is dissolved in Coupling Buffer (0.1M NaHCO$_3$, pH 8.3, containing 0.5M NaCl) containing EDTA. The gel is washed with Coupling Buffer, the excess is removed by suction, and the enzyme solution is mixed with the gel. The mixture is allowed to stand overnight at 4° C. without stirring. The gel is then placed in a Blocking Buffer containing 1M ethanolamine, pH 8.0, for 2 hr at room temperature. The gel is then washed with the Coupling Buffer, 0.1M Acetate Buffer, pH 4.0, containing 0.5M NaCl, and washed twice with Coupling Buffer. The enzyme protein-SEPHAROSE conjugate is now ready for use and can be stored at 4° to 8° C. Cyanogen bromide can be added to the buffer solution as a bacteriostat.

3. The column is equilibrated with from 2 to 3 volumes of buffer (0.15M PBS, pH 7.2), and the sample is then applied to the column. The eluted fractions containing antibody are collected until peak activity disappears. The column is washed with 10×volumes of 0.15 PBS buffer, pH 7.2.

4. The column is then washed to desorb immunoaffinity bound antibody. The peak fractions are dialyzed against 0.15M PBS, pH 7.2, for 24–36 hr at 4° C. with multiple buffer changes.

EXAMPLE 7

Polyclonal Anti-(MI-$D_B$) Antibodies

Polyclonal antiserum against MI-$D_B$ antigen, prepared in accordance with the procedure of Example 5, is elicited in rabbits using the immunization techniques and schedules described in Example 6. The antiserum is screened in a solid phase assay similar to that of Example 6, substituting MI-D. for MI-$P_A$, to yield polyclonal anti-(MI-$D_B$) antibodies.

EXAMPLE 8

Preparation of Polyclonal Anti-(CK-MM) Antibodies

Purified CK-MM isoenzyme (Diagnostic Biochemicals Laboratories, Dallas, Tex.), 250 µg (micrograms), in Freund's adjuvant is used to immunize rabbits or goats, with injections at two week intervals. Test bleeds are checked for antibody activity after ten weeks of immunization. Antiserum is collected over several months until an acceptable antibody titer is obtained. The polyclonal antibody is purified generally according to the procedures of Gomez and Wicks, U.S. Pat. No. 4,353,982. The antibodies react to all isoforms of CK-MM, CK-$MM_A$, CK-$MM_B$, and CK-$MM_C$, and other proteins present as contaminants.

EXAMPLE 9

Preparation of Polyclonal Anti-(CK-MM isoform) Antibodies

CK-$MM_A$ isoform are obtained from total CK-MM heart extract by the method of Vaidya et al, *Biochimica et Biophysica Acta.* 790:230–237 (1984). CK-$MM_B$ isoform and CK-$MM_C$ isoform are obtained by the methods of Vaidya (supra) followed by conversion of CK-$MM_A$ to CK-$MM_B$ and CK-$MM_C$ by the methods of Perryman et al, *Clin. Chem.* 30:662 (1984). The procedure of Example 6 is repeated, substituting the MI-P antigen respectively with the CK-$MM_A$ isoform, the CK-$MM_B$ isoform, and the CK-$MM_C$ isoform to yield antisera containing a mixture of anti-(CK-MM) antibodies.

The column of Step 3 of Example 6 is washed with 10×volumes of 0.15 PBS buffer, pH 7.2. The column is then washed with distilled water to desorb immunoaffinity bound antibody. HPLC grade distilled water is perfused through the column in a volume equal to the void volume, and elution is stopped for 6 hr. The column is then eluted with additional distilled water at a rate of 15–20 ml/hr, collecting the eluted samples and retaining peak fractions. The peak fractions are dialyzed against 0.15 M PBS, pH 7.2, for 24–36 hr at 4° C. with multiple buffer changes.

To separate anti-(CK-$MM_A$) antibodies, this procedure is repeated with the eluant using affinity columns to which CK-$MM_B$, CK-$MM_C$ and CK-MB are bound, to yield an ultimate eluant containing anti-(CK-$MM_A$) antibodies which do not significantly bind with CK-$MM_A$, CK-$MM_C$ and CK-MB isoforms.

To separate anti-(CK-$MM_C$) antibodies, this procedure is repeated with the eluant with affinity columns to which CK-$MM_A$, CK-$MM_C$ and CK-MB is bound, to yield an ultimate eluant containing anti-(CK-$MM_B$) antibodies which do not significantly bind with CK-$MM_A$, CK-$MM_C$ and CK-MB isoforms.

To separate anti-(CK-$MM_C$) antibodies, this procedure is repeated with the eluant with affinity columns to which CK-$MM_A$, CK-$MM_B$ and CK-MB is bound, to yield an ultimate eluant containing anti-(CK-$MM_C$) antibodies which do not significantly bind with CK-$MM_A$, CK-$MM_B$ and CK-MB isoforms.

EXAMPLE 10

Preparation of Monoclonal Anti-(CK-MM isoform) Antibodies

The immunization protocol of Example 2 is repeated, replacing the CK-MM isoform fraction with purified CK-MM isoform emulsified in complete Freund's adjuvant. CK-$MM_A$ is prepared by the method of Vaidya et al, *Biochimica et Biophysica Acta.* 790:230–237 (1984). CK-$MM_B$ isoform and CK-$MM_C$ isoform are obtained by the methods of Vaidya (supra) followed by conversion of CK-$MM_A$ to CK-$MM_B$ and CK-$MM_C$ by the methods of Perryman et al, *Clin. Chem.* 30:662 (1984). The cell fusion and screening procedures of Example 2 are repeated, with screening for antibodies specific for CK-MM using solid-phase radioimmunoassay on post fusion day 8. Culture expansion, hybridoma cloning, ascite production and purification of monoclonal antibodies similarly follow the procedures of Example 2. Screening of antibodies generally follow the procedures of Example 9. Antibodies to CK-MM$_A$, CK-MM$_B$, CK-MM$_C$, CK-MM$_{A+B}$, CK-MM$_{A+C}$, and CK-MM$_{B+C}$ are produced.

EXAMPLE 11

Radioactive Labeling of Polyclonal and Monoclonal Antibodies

Polyclonal and monoclonal antibodies are labeled with $^{125}$I using the "Iodogen" method of Fraker et al, Biochem. Biophys. Res. Commun. 80:849 (1978), modified as described in U.S. Pat. No. 4,624,916, the contents of which are hereby incorporated by reference in their entirety.

EXAMPLE 12

Immobilization of Magnetizable Particles

Magnetizable particles were obtained from Seradyne, Inc. (Indianapolis, Ind. 46266). Monoclonal antibodies were immobilized on these particles by a combination of passive absorption and immunochemical immobilization techniques, modified from Tijssen, PRACTICE AND THEORY OF ENZYME IMMUNOASSAYS. Elsevier Science Publishers B.V. (1985), pp. 301–311, the contents of which are hereby incorporated by reference in their entirety.

EXAMPLE 13

Test method using magnetizable particles

A clinical chemistry spectrophotometer, ABA-100 (Abbott Laboratories, North Chicago, Ill. 60048) was used with CK-substrate (Boehringer-Mannheim).

The enzymatic activity of CK in a first portion of a test sample was determined. Another portion of the test sample was reacted with a solid-phase reagent composed of 0.01 μg of magnetizable particles on which goat anti-(mouse IgG) antibody was immobilized. A dilution of monoclonal antibody specific for CK-MM$_C$ (derived from hybridoma ATCC HB9914) was added to the particles prior to reaction with the sample. After the reaction, the particles were allowed to settle, and enzymatic activity of the supernatant was measured. The difference in the two activity measurements was proportional to the amount of CK-MM removed. The ratio of CK-MM$_C$:Total CK can be used to asses the lapse of time since the occurrence of an AMI. The ratio is small when the infarction is recent.

EXAMPLE 14

Suggested Diagnosis Using MI-D$_B$ Antibody

The following test results show the clinical utility of measuring the MI-DB analyte using the anti-(MI-D$_B$) antibody. Serial specimens were collected from patients suspected of having a myocardial infarction and tested with the immunoradiometric QUICK-MB assay described in U.S. Pat. No. 4,624,916 (International Immunoassay Laboratories, Inc., 1900 Wyatt Drive, Santa Clara, Calif. 95054). An electrophoresis method was used to detect LD abnormality. Inversion of the ratio of isoenzyme fractions 1 and 2 of LD was taken as the late indication of acute infarction. The transient increase in CK-MB above 3.3 EU/L is suggestive of acute myocardial infarction. The analyte MI-D$_B$ concentration of 20% (=200 EU/L) is abnormal.

The procedures of Example 13 are followed with the exception that the antibody concentration is limiting.

TABLE D

| Patient ID | Time of Sample | CK-MB, EU/L | MI-D$_B$ binding[a] |
|---|---|---|---|
| A[b] | 02/19/87 4 AM | 2.4 (nor.) | 87.8 (elev.) |
| | 02/20/87 4 AM | 20.4 | 63.5 |
| B[c] | 02/17/87 4 PM | >40.0 | 78.9 |
| | 02/17/87 11 PM | 31.0 | 48.9 |
| | 02/18/87 8 AM | 17.0 | 23.4 |
| | 02/18/87 6 PM | 8.6 | 32.6 (incr.) |
| | 02/21/87 9 PM | 2.6 (nor.) | 46.3 |
| | 02/22/87 Midnight | 2.9 | 24.0 |
| | 02/22/87 5 AM | 7.1 | 37.7 |
| | 02/22/87 4 AM | 10.4 | 25.9 |
| C[d] | 02/24/87 1 PM | 2.6 (nor.) | 23.9 (elev.) |
| | 02/24/87 5 PM | 12.7 | 34.9 |
| | 02/25/87 Midnight | 32.6 | 40.7 |
| | 02/25/87 5 AM | >40.0 | 56.9 |
| | 02/25/87 8 AM | >40.0 | 56.3 |
| | 02/25/87 11 AM | 10.0 | 72.7 |
| D[e] | 02/19/87 4 PM | 2.5 (nor.) | 32.6 (abnor) |
| | 02/20/87 1 AM | 3.2 (nor.) | 31.2 |

[a]% of highest calibrator, about equal to 1000 EU/L
[b]Possible reinfarction detected earlier by MI-D$_B$ as compared to CK-MB.
[c]Patient undergoing reinfarction, detected earlier by MI-D$_B$ while CK-MB level is still descending.
[d]Early detection by MI-D$_B$.
[e]Patient had LD isoenzyme abnormality (LD) flip, indicating delayed recognition of AMI. Sample normal by CK-MB measurement, abnormal by MI-D$_B$ measurement.

EXAMPLE 15

Sandwich Immunoassay

The procedure of Example 14 is repeated with a limiting amount of immobilized primary antibody. This sandwich immunoassay is designed for detection of recent infarction only. The amount of immobilized primary antibody, anti-(MI-P$_A$) antibody, is limiting and designed to accommodate only low levels of MI-P$_A$. Normally, MI-P$_A$ is not present in patient serum, or is present in such low levels as to be effectively absent. During the early phase of the infarction, the level of MI-P$_A$ increases. Because of the assay design, as the level of MI-P increases, increasing amounts of it will remain in the liquid phase since the solid phase becomes saturated. The secondary antibody is $^{125}$I-labeled MI-D$_B$, the anti-(MI-D$_B$) antibody produced in accordance with the procedure of Example 11.

When the solid phase is capable of binding all MI-P$_A$, there is no excess in the liquid phase, and all of the labeled anti-(MI-D$_B$) antibody is available to bind the solid phase. As the level of CK increases, increasing amounts of the labeled antibody will remain in the liquid phase. This design gives a high level of bound activity only when the level of the analyte pair is high, and the level of total CK is low. The following results were obtained:

TABLE E

| MI-D$_B$ % of highest calibrator | Bound Counts per min | | | | |
|---|---|---|---|---|---|
| | Total Activity, IU/L | | | | |
| | 62.5 | 125 | 250 | 500 | 1000 |
| 0 | 1556 | 1553 | 1695 | 1819 | 2708 |
| 20 | 7067 | 11920 | 18290 | 24800 | 23071 |
| 40 | 11673 | 18641 | 23275 | 22017 | 17651 |
| 50 | 13309 | 19802 | 23079 | 21330 | 15849 |
| 60 | 16339 | 21991 | 22774 | 20280 | |
| 80 | 18744 | 23242 | 22800 | 17802 | |

TABLE E-continued

| MI-D$_B$ % of highest calibrator | Bound Counts per min | | | |
|---|---|---|---|---|
| | Total Activity, IU/L | | | |
| | 62.5 | 125 | 250 | 500 | 1000 |
| 100 | 20824 | 23468 | 20974 | 16445 | |

As can be seen, the maximum counts per minute, at any given percent level of the analyte pair, occurs at a level of total CK. Any further rise in total MI would cause a decrease in counts.

EXAMPLE 16

CK-MM$_C$ Immunoassay

Monoclonal anti-(CK-MM$_C$) antibody, produced by the hybridoma ATCC HB9914 is used as the primary antibody to determine CK-MM$_C$ in a plasma sample. The secondary antibody is labeled goat anti-(CK-MM) antibody. In an assay to determine total CK-MM, rabbit anti-(CK-MM) is the primary antibody, and the secondary antibody is labeled goat anti-(CK-MM) antibody. The results shown in Table F were obtained. As expected, the percentage of CK-MM$_C$ increased as the total CK-MM decreased.

TABLE F

| Patient ID | Total CK | CK-MB, EU/L | CK-MM$_C$ | Ratio of CK-MM/CK-MM$_C$ by Electrophoresis |
|---|---|---|---|---|
| A[a] | 1131 | 37.4 | 27.0 | 2.77 |
| | — | — | 65.8 | 1.99 |
| | 1272 | 36.7 | 61.5 | .83 |
| | 875 | 23.7 | 77.2 | .48 |
| B[b] | 135 | 4.8 | 9.0 | 1.1 |
| | 125 | 4.1 | 76.0 | .6 |
| | 87 | 2.6 | 52.0 | .2 |
| C[b] | 309 | 10.2 | 18.0 | 1.0 |
| | 1325 | 39.7 | 7.0 | 2.5 |
| | 1445 | 24.2 | 38.0 | .2 |
| D[a] | 731 | 14.4 | 21.0 | .3 |
| | 476 | 7.5 | 25.0 | .3 |
| | 268 | 4.4 | 34.0 | .2 |
| E[a] | 2010 | 25.2 | 33.0 | .2 |
| | 758 | 4.5 | 62.0 | .02 |
| | 194 | — | 55.0 | .02 |

[a]High CK-MB values and decreasing electrophoretic ratios from these high values, seen with patients A, D and E, represent later stages of infarction.
[b]Low total percentage of CK-MM$_C$ were seen in patients B and C, with early stages of infarction.

EXAMPLE 17

CK-MB$_B$ Immunoassay

A dilution of monoclonal antibody specific for CK-MB$_B$ (derived from hybridoma ATCC HB9914) was added to magnetizable particles on which goat anti-(mouse IgG) antibody was immobilized. A dilution of monoclonal antibody specific for CK-MM (commercially available from International Immunoassay Laboratories, Inc., Santa Clara Calif.) was added to another aliquot of magnetizable particles on which goat anti-(mouse IgG) antibody was immobilized. Anti-(CK-BB) antibody (commercially available from International Immunoassay Laboratories, Inc., Santa Clara Calif.) was labeled with I$^{125}$ as described in Example 11. Anti-(CK-MM) antibodies and anti-(CK-BB) antibodies bind both the CK-MB$_A$ and the CK-MB$_B$ isoforms and function in the assay as anti-(CK-MB$_{A+B}$) antibodies.

One portion of the test sample was reacted with a solid-phase reagent composed of 250 μl of magnetizable particles coated with anti-(CK-MM) and with 100 μl of $^{125}$I-anti-(CK-BB) antibody to determine the concentration of CK-MB$_{A+B}$. Another portion of the test sample was reacted with a solid-phase reagent composed of 250 μl of magnetizable particles coated with anti-(CK-MB$_B$) and with 100 μl of I$^{125}$-anti-(CK-BB) antibody to determine the concentration of CK-MB$_B$. After 20 minutes, the particles were allowed to settle, the supernatant was aspirated, and bound counts were measured. The ratio of CK-MB$_B$:Total CK-MB (CK-MB$_{A+B}$) can be used to asses the lapse of time since the occurrence of an AMI. The ratio is small when the infarction is recent.

We claim:

1. An immunological method for determining the time of occurrence of an acute myocardial infarction in a patient, where infarction is associated with an increase in the body fluid concentration of a CK-MB species selected from the group consisting of
   a first CK-MB isoform having a C-terminal lysine on the M subunit,
   a second CK-MB isoform produced by in vivo loss of the C-terminal lysine from the M subunit of the first isoform, wherein the loss of the C-terminal lysine alters a first epitope on the first isoform to produce a second epitone on the second isoform, and
   total CK-MB,
   wherein the concentrations of the CK-MB species in the body fluid change in a known pattern with time, comprising the steps of:
   (1) determining the concentration A of a first selected species in the body fluid,
   (2) determining the concentration B of a second selected species different from the first selected species in the body fluid,
   wherein one of the first and second determining steps comprises detecting the amount of said first or second CK-MB isoform in the body fluid by contacting the body fluid with an antibody that specifically binds to the first or second epitope of said first or second CK-MB isoform, and
   (3) correlating any change in the concentration A or B with the known pattern of concentration change to determine the time of occurrence of the infarction.

2. The method of claim 1, wherein said detecting step comprises contacting the body fluid with an antibody that specifically binds said first epitope of said first CK-MB isoform, but does not specifically bind with said second epitope of said second CK-MB isoform.

3. The method of claim 1, wherein said detecting step comprises contacting the body fluid with an antibody that specifically binds said second epitope of said second CK-MB isoform, but does not specifically bind said first epitope of said first CK-MB isoform.

4. An antibody which specifically binds a CK-MB isoform having a C-terminal lysine on the M subunit, but said antibody does not specifically bind said isoform after loss of said C-terminal lysine.

5. An antibody which specifically binds a CK-MB isoform lacking a C-terminal lysine on the M subunit, but said antibody does not specifically bind a CK-MB isoform having a C-terminal lysine on the M subunit.

6. An immunological method for determining the amount of a CK-MB isoform having a C-terminal lysine on the M subunit in a sample, comprising contacting the sample with an antibody which specifically binds said isoform, but does not specifically bind said isoform after the loss of said C-terminal lysine on said M subunit, and determining the amount of CK-MB isoform bound with said antibody.

7. An immunological method for determining the amount of a CK-HB isoform lacking a C-terminal lysine on the M subunit in a sample, comprising contacting the sample with an antibody which specifically binds said isoform, but does not specifically bind a CK-MB isoform having a C-terminal lysine on said subunit, and determining the amount of CK-MB isoform bound with said antibody.

8. An immunoextraction method for determining the amount of a CK-MB isoform having a C-terminal lysine on the M subunit, in a sample, comprising the steps of:

contacting said sample with an antibody which specifically binds the M subunit lacking a C-terminal lysine, but does not specifically bind said isoform having said C-terminal lysine on said M subunit, said antibody being immobilized on a solid support, separating said solid support having bound thereto said CK-MB isoform lacking a C-terminal lysine on the M subunit from said sample, and measuring the amount of said CK-MB isoform having a C-terminal lysine on the M subunit remaining in said sample.

9. An immunoextraction method for determining the amount of a CK-MB isoform lacking a C-terminal lysine on the M subunit, in a sample, comprising the steps of:

contacting said sample with an antibody which specifically binds the M subunit having a C-terminal lysine, but does not specifically bind said isoform after loss of said C-terminal lysine on said M subunit, said antibody being immobilized on a solid support, separating said solid support having bound thereto said CK-MB isoform having a C-terminal lysine on the M subunit from said sample, and measuring the amount of said CK-MB isoform lacking a C-terminal lysine on the M subunit remaining in said sample.

* * * * *